US011185073B2

(12) United States Patent
Weiss et al.

(10) Patent No.: US 11,185,073 B2
(45) Date of Patent: Nov. 30, 2021

(54) MICROBIOCIDAL QUINOLINE (THIO)CARBOXAMIDE DERIVATIVES

(71) Applicant: SYNGENTA PARTICIPATIONS AG, Basel (CH)

(72) Inventors: Matthias Weiss, Stein (CH); Laura Quaranta, Stein (CH); Farhan Bou Hamdan, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 16/641,151

(22) PCT Filed: Aug. 16, 2018

(86) PCT No.: PCT/EP2018/072273
§ 371 (c)(1),
(2) Date: Feb. 21, 2020

(87) PCT Pub. No.: WO2019/038189
PCT Pub. Date: Feb. 28, 2019

(65) Prior Publication Data
US 2020/0170250 A1 Jun. 4, 2020

(30) Foreign Application Priority Data
Aug. 23, 2017 (EP) ..................................... 17187422

(51) Int. Cl.
*C07D 215/54* (2006.01)
*A01N 43/42* (2006.01)

(52) U.S. Cl.
CPC ........... *A01N 43/42* (2013.01); *C07D 215/54* (2013.01)

(58) Field of Classification Search
CPC ............................... A01N 43/42; C07D 215/54
See application file for complete search history.

(56) References Cited

U.S. PATENT DOCUMENTS

| | | | | |
|---|---|---|---|---|
| 2020/0022368 A1* | 1/2020 | Quaranta | ............... | A01N 43/42 |
| 2020/0260728 A1* | 8/2020 | Bou Hamdan | ........ | A01N 43/42 |
| 2020/0267978 A1* | 8/2020 | Weiss | .................... | A01N 43/42 |
| 2020/0281201 A1* | 9/2020 | Bou Hamdan | ...... | C07D 215/16 |

FOREIGN PATENT DOCUMENTS

WO 2003080577 A2 10/2003
WO 2004039783 A1 5/2004

OTHER PUBLICATIONS

Wermuth, Comprehensive Medicinal Chemistry, II, 2007 figure 26, 2.16.2.2.3 Carboxamide Bioisosteres. (Year: 2007).*
ISR and Written Opinion for PCT/EP2018/072273, dated Oct. 10, 2018.
Extended European Search report of EP No. 17187422.5 dated Oct. 6, 2017.
Shikha Kumari et al., Amide Bond Bioisosteres: Strategies, Synthesis, and Success, J. Med. Chem, 2020, vol. 63, pp. 12290-12358.
George A. Patani et al., Bioisosterism: A Rational Approach in Drug Design, Chemical Reviews, 1996, vol. 96, No. 8, pp. 3147-3176.
Corinne Beinat et al., Investigations of Amide Bond Variation and Biaryl Modification in Analogues of α7 nAChR Agonist SEN12333, European Journal of Medicinal Chemistry, vol. 84, 2014, pp. 200-205.
Kshitij Verma et al., Potent and Highly Selective Aldo-Keto Reductase 1C3 (AKR1C3) Inhibitors Act as Chemotherapeutic Potentiators in Acute Myeloid Leukemia and T-Cell Acute Lymphoblastic Leukemia, J Med Chem, 2019, vol. 62, No. 7, pp. 3590-3616.
Mario de la Fuente Revenga et al., Novel N-Acetyl Bioisosteres of Melatonin: Melatonergic Receptor Pharmacology, Physicochemical Studies, and Phenotypic Assessment of Their Neurogenic Potential, J. Med. Chem., 2015, vol. 58, No. 14, pp. 4998-5014.
Musiol, R. et al., Quinoline-Based Antifungals, Current Medicinal Chemistry, 2010, vol. 17, pp. 1960-1973.
Indian Examination Report for Indian Application No. 202017005926, dated Sep. 1, 2021.

* cited by examiner

*Primary Examiner* — D Margaret M Seaman
(74) *Attorney, Agent, or Firm* — Bakerhostetler; Toni-Junell Herbert

(57) ABSTRACT

Compounds of the formula (I) wherein the substituents are as defined in claim 1. Furthermore, the present invention relates to agrochemical compositions which comprise compounds of formula (I), to preparation of these compositions, and to the use of the compounds or compositions in agriculture or horticulture for combating, preventing or controlling infestation of plants, harvested food crops, seeds or non-living materials by phytopathogenic microorganisms, in particular fungi.

19 Claims, No Drawings

MICROBIOCIDAL QUINOLINE (THIO)CARBOXAMIDE DERIVATIVES

CROSS-REFERENCE TO RELATED APPLICATIONS

This application is a 371 National Stage application of International Application No. PCT/EP2018/072273 filed Aug. 16, 2018 which claims priority to EP 17187422.5, filed Aug. 23, 2017, the entire contents of which applications are hereby incorporated by reference.

The present invention relates to microbiocidal quinoline (thio)carboxamide derivatives, e.g. as active ingredients, which have microbiocidal activity, in particular fungicidal activity. The invention also relates to preparation of these quinoline (thio)carboxamide derivatives, to intermediates useful in the preparation of these quinoline (thio)carboxamide derivatives, to the preparation of these intermediates, to agrochemical compositions which comprise at least one of the quinoline (thio)carboxamide derivatives, to preparation of these compositions and to the use of the quinoline (thio)carboxamide derivatives or compositions in agriculture or horticulture for controlling or preventing infestation of plants, harvested food crops, seeds or non-living materials by phytopathogenic microorganisms, in particular fungi.

Certain fungicidal quinoline (thio)carboxamide compounds are described in WO04039783.

It has now surprisingly been found that certain novel quinoline (thio)carboxamide derivatives have favourable fungicidal properties.

The present invention therefore provides compounds of formula (I)

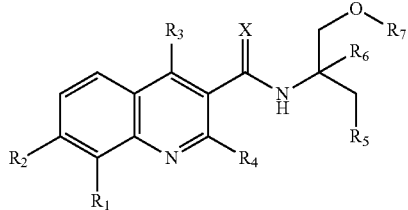

wherein
X is O or S;
$R_1$ is hydrogen, halogen, methyl or cyano;
$R_2$ is hydrogen, methyl or halogen;
$R_3$ and $R_4$ are each independently selected from hydrogen, halogen and methyl;
$R_5$ is $C_1$-$C_4$ alkyl, $C_1$-$C_2$ haloakyl, $C_2$-$C_4$ alkenyl or $C_3$-$C_6$ cycloalkyl, wherein the alkyl, alkenyl and cycloalkyl may be optionally substituted with 1 to 3 substituents independently selected from halogen, cyano, $C_1$-$C_3$ alkyl, $C_1$-$C_3$ alkoxy and $C_1$-$C_3$ alkylthio;
$R_6$ is hydrogen, cyano or $C_1$-$C_4$ alkyl;
$R_7$ is $C_1$-$C_5$ alkyl, $C_3$-$C_7$ cycloalkyl, $C_3$-$C_5$ alkenyl, $C_3$-$C_6$ cycloalkenyl, $C_3$-$C_5$ alkynyl, a $C_5$-$C_{10}$ saturated or partially unsaturated bicyclic carbocycle, aryl, aryl($C_1$-$C_4$)alkyl, a saturated or partially unsaturated heterocycle or heteroaryl, wherein the alkyl, cycloalkyl, alkenyl, cycloalkenyl, bicyclic carbocycle, alkynyl, may be optionally substituted with one or more substituents independently selected from halogen, cyano, $C_1$-$C_3$ alkyl, $C_1$-$C_3$ alkoxy, $C_1$-$C_3$ alkylthio; $C_1$-$C_3$ haloalkoxy, $C_1$-$C_3$ haloalkylthio, $C_3$-$C_5$ cycloalkyl or phenyl, and wherein the aryl, heterocycle or heteroaryl may be optionally substituted with one or more substituents independently selected from halogen, cyano, $C_1$-$C_3$ alkyl, $C_1$-$C_3$ alkoxy, $C_1$-$C_3$ alkylthio; $C_1$-$C_3$ haloalkoxy, $C_1$-$C_3$ haloalkylthio or $C_3$-$C_5$ cycloalkyl;
and salts and/or N-oxides thereof.

In a second aspect the present invention provides an agrochemical composition comprising a compound of formula (I).

Compounds of formula (I) may be used to control phytopathogenic microorganisms. Thus, in order to control a phytopathogen a compound of formula (I), or a composition comprising a compound of formula (I), according to the invention may be applied directly to the phytopathogen, or to the locus of a phytopathogen, in particular to a plant susceptible to attack by phytopathogens.

Thus, in a third aspect the present invention provides the use of a compound of formula (I), or a composition comprising a compound of formula (I), as described herein to control a phytopathogen.

In a further aspect the present invention provides a method of controlling phytopathogens, comprising applying a compound of formula (I), or a composition comprising a compound of formula (I), as described herein to said phytopathogen, or to the locus of said phytopathogen, in particular to a plant susceptible to attack by a phytopathogen.

Compounds of formula (I) are particularly effective in the control of phytopathogenic fungi.

Thus, in a yet further aspect the present invention provides the use of a compound of formula (I), or a composition comprising a compound of formula (I), as described herein to control phytopathogenic fungi.

In a further aspect the present invention provides a method of controlling phytopathogenic fungi, comprising applying a compound of formula (I), or a composition comprising a compound of formula (I), as described herein to said phytopathogenic fungi, or to the locus of said phytopathogenic fungi, in particular to a plant susceptible to attack by phytopathogenic fungi.

Where substituents are indicated as being optionally substituted, this means that they may or may not carry one or more identical or different substituents, e.g. one to four substituents. Normally not more than three such optional substituents are present at the same time. Preferably not more than two such optional substituents are present at the same time (i.e. the group may be optionally substituted by one or two of the substituents indicated as "optional"). Where the "optional substituent" group is a larger group, such as cycloalkyl or phenyl, it is most preferred that only one such optional substituent is present. Where a group is indicated as being substituted, e.g. alkyl, this includes those groups that are part of other groups, e.g. the alkyl in alkylthio.

The term "halogen" refers to fluorine, chlorine, bromine or iodine, preferably fluorine, chlorine or bromine.

Alkyl substituents (either alone or as part of a larger group, such as alkoxy-, alkylthio-) may be straight-chained or branched. Alkyl on its own or as part of another substituent is, depending upon the number of carbon atoms mentioned, for example, methyl, ethyl, n-propyl, n-butyl, n-pentyl, n-hexyl and the isomers thereof, for example, iso-propyl, iso-butyl, sec-butyl, tert-butyl or iso-amyl.

Alkenyl substituents (either alone or as part of a larger group, eg. alkenyloxy) can be in the form of straight or branched chains, and the alkenyl moieties, where appropriate, can be of either the (E)- or (Z)-configuration. Examples are vinyl and allyl. The alkenyl groups are preferably $C_2$-$C_6$, more preferably $C_2$-$C_4$ and most preferably $C_2$-$C_3$ alkenyl groups.

Alkynyl substituents (either alone or as part of a larger group, eg. alkynyloxy) can be in the form of straight or branched chains. Examples are ethynyl and propargyl. The alkynyl groups are preferably $C_2$-$C_6$, more preferably $C_2$-$C_4$ and most preferably $C_2$-$C_3$ alkynyl groups.

Cycloalkyl substituents may be saturated or partially unsaturated, preferably fully saturated, and are, for example, cyclopropyl, cyclobutyl, cyclopentyl or cyclohexyl.

Saturated bicyclic carbocycles are, for example, bicyclo[1.1.1]pentane, bicyclo[2.1.1]hexane, bicyclo[2.2.1]heptane, bicyclo[2.2.2]octane, bicyclo[2.1.0]pentane, bicyclo[3.1.0]hexane, bicyclo[4.1.0]heptane, bicyclo[5.1.0]octane, bicyclo[2.2.0]hexane, bicyclo[3.2.0]heptane, bicyclo[4.2.0]octane, octahydropentalene, octahydroindene, decalin, bicyclo[3.2.1]octane, bicyclo[3.1.1]heptane, decahydroazulene, bicyclo[3.3.1]nonane. Preferred saturated bicyclic carbocycles are bicyclo[2.2.1]heptane, bicyclo[3.1.0]hexane, bicyclo[4.1.0]heptane and bicyclo[3.2.0]heptane. Most preferred are bicyclo[2.2.1]heptane and bicyclo[3.1.0]hexane.

Partially unsaturated bicyclic carbocycles are, for example, bicyclo[2.2.1]heptane, bicyclo[2.2.2]octane, bicyclo[3.1.0]hexane, bicyclo[4.1.0]heptene, bicyclo[5.1.0]octene, bicyclo[3.2.0]heptene, bicyclo[4.2.0]octene, bicyclo[3.1.1]heptene, hexahydropentalene, tetrahydropentalene, bicyclo[3.2.1]octene, hexahydroindene, tetrahydroindene, indane, tetrahydronapthalene and dihydronapthalene. Preferred unsaturated bicyclic carbocycles are bicyclo[2.2.1]heptane, indane and tetrahydronaphthalene. Most preferred are indane and tetrahydronapthalene.

Haloalkyl groups (either alone or as part of a larger group, eg. haloalkyloxy) may contain one or more identical or different halogen atoms and, for example, may stand for $CH_2Cl$, $CHCl_2$, $CCl_3$, $CH_2F$, $CHF_2$, $CF_3$, $CF_3CH_2$, $CH_3CF_2$, $CF_3CF_2$ or $CCl_3CCl_2$.

Haloalkenyl groups (either alone or as part of a larger group, eg. haloalkenyloxy) are alkenyl groups, respectively, which are substituted with one or more of the same or different halogen atoms and are, for example, 2,2-difluoro-vinyl or 1,2-dichloro-2-fluoro-vinyl.

Haloalkynyl groups (either alone or as part of a larger group, eg. haloalkynyloxy) are alkynyl groups, respectively, which are substituted with one or more of the same or different halogen atoms and are, for example, 1-chloro-prop-2-ynyl.

Alkoxy means a radical —OR, where R is alkyl, e.g. as defined above. Alkoxy groups include, but are not limited to, methoxy, ethoxy, 1-methylethoxy, propoxy, butoxy, 1-methylpropoxy and 2-methylpropoxy.

Cyano means a —CN group.

Amino means an —$NH_2$ group.

Hydroxyl or hydroxy stands for a —OH group.

Aryl groups (either alone or as part of a larger group, such as e.g. aryloxy, aryl-alkyl) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

Heteroaryl groups (either alone or as part of a larger group, such as e.g. heteroaryloxy, heteroaryl-alkyl) are aromatic ring systems containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl (e.g. [1,2,4] triazolyl), furanyl, thiophenyl, oxazolyl, isoxazolyl, oxadiazolyl, thiazolyl, isothiazolyl and thiadiazolyl. Examples of bicyclic groups include purinyl, quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

Heterocyclyl groups, heterocycles or heterocyclic rings (either alone or as part of a larger group, such as heterocyclyl-alkyl) are non-aromatic ring structures containing up to 10 atoms including one or more (preferably one, two or three) heteroatoms selected from O, S and N. Examples of monocyclic groups include, oxetanyl, 4,5-dihydro-isoxazolyl, thietanyl, pyrrolidinyl, tetrahydrofuranyl, [1,3]dioxolanyl, piperidinyl, piperazinyl, [1,4]dioxanyl, imidazolidinyl, [1,3,5]oxadiazinanyl, hexahydro-pyrimidinyl, [1,3,5]triazinanyl and morpholinyl or their oxidised versions such as 1-oxo-thietanyl and 1,1-dioxo-thietanyl. Examples of bicyclic groups include 2,3-dihydro-benzofuranyl, benzo[1,4]dioxolanyl, benzo[1,3]dioxolanyl, chromenyl, and 2,3-dihydro-benzo[1,4]dioxinyl. Where a heterocyclyl moiety is said to be substituted, the heterocyclyl moiety is preferably substituted by one to four substituents, most preferably by one to three substituents.

The presence of one or more possible asymmetric carbon atoms in a compound of formula (I) means that the compounds may occur in optically isomeric forms, i.e. enantiomeric or diastereomeric forms. Also atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers. The present invention includes all possible tautomeric forms for a compound of formula (I).

In each case, the compounds of formula (I) according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

Preferred values of X, $R_1$, $R_2$, $R_3$, $R_4$, $R_5$, $R_6$ and $R_7$ are, in any combination thereof, as set out below:

Preferably X is O.

Preferably $R_1$ is hydrogen, fluoro, chloro, bromo or methyl.

More preferably $R_1$ is fluoro, chloro or methyl.

Most preferably $R_1$ is fluoro or methyl.

Preferably $R_2$ is hydrogen, methyl, chloro or fluoro.

More preferably $R_2$ is hydrogen or fluoro.

Most preferably $R_2$ is hydrogen.

Preferably $R_3$ and $R_4$ are each independently selected from hydrogen, chloro and methyl.

More preferably $R_3$ and $R_4$ are each independently selected from hydrogen and methyl.

Even more preferably $R_3$ is methyl and $R_4$ is hydrogen; or $R_3$ is hydrogen and $R_4$ is methyl; or $R_3$ is hydrogen and $R_4$ is hydrogen.

Most preferably $R_3$ and $R_4$ are both hydrogen Preferably $R_5$ is $C_1$-$C_4$ alkyl, $C_1$-$C_2$ haloakyl, $C_2$-$C_4$ alkenyl or $C_3$-$C_6$ cycloalkyl, wherein the alkyl, alkenyl and cycloalkyl may be optionally substituted with 1 to 3 substituents independently selected from fluoro, cyano, methyl, methoxy and methylthio.

More preferably $R_5$ is $C_1$-$C_4$ alkyl, $C_1$-haloakyl, $C_2$-$C_4$ alkenyl or $C_3$-$C_4$ cycloalkyl, wherein the alkyl, alkenyl and cycloalkyl may be optionally substituted with 1 to 3 substituents independently selected from fluoro, cyano and methyl.

Even more preferably $R_5$ is $C_1$-$C_4$ alkyl, trifluoromethyl, $C_2$-$C_4$ alkenyl or $C_3$-$C_4$ cycloalkyl, wherein the alkyl, alkenyl and cycloalkyl may be optionally substituted with 1 to 3 fluorine atoms or a methyl.

Most preferably $R_5$ is ethyl, n-propyl, iso-propyl, n-butyl, sec-butyl, iso-butyl, tert-butyl or trifluoromethyl.

Preferably $R_6$ is hydrogen or $C_1$-$C_3$ alkyl.

More preferably $R_6$ is hydrogen, methyl or ethyl.

Most preferably $R_6$ is methyl.

Preferably $R_7$ is $C_1$-$C_5$ alkyl, $C_3$-$C_7$ cycloalkyl, $C_3$-$C_5$ alkenyl, $C_3$-$C_6$ cycloalkenyl, $C_3$-$C_5$ alkynyl, a $C_5$-$C_{10}$ saturated bicyclic carbocycle, a $C_5$-$C_{10}$ partially unsaturated bicyclic carbocycle, phenyl, phenyl($C_1$-$C_3$)alkyl, oxetanyl, tetrahydrofuranyl, tetrahydropyranyl, pyridinyl, thiophenyl, thiazolyl, oxazolyl or pyrazolyl, wherein the alkyl, cycloalkyl, alkenyl, cycloalkenyl, carbocycle and alkynyl may be optionally substituted with one or more substituents independently selected from fluoro, chloro, cyano, methyl, methoxy, methylthio; $C_1$-$C_2$ fluoroalkoxy, $C_1$-$C_2$ fluoroalkylthio, cyclopropyl and cyclobutyl, and wherein the phenyl, oxetanyl, tetrahydrofuranyl, tetrahydropyranyl, pyridinyl, thiophenyl, thiazolyl, oxazolyl and pyrazolyl may be optionally substituted with one or more substituents independently selected from fluoro, chloro, cyano, methyl, methoxy, methylthio; $C_1$-$C_2$ fluoroalkoxy, $C_1$-$C_2$ fluoroalkylthio, cyclopropyl and cyclobutyl.

More preferably $R_7$ is $C_1$-$C_5$ alkyl, $C_3$-$C_7$ cycloalkyl, $C_3$-$C_4$ alkenyl, $C_3$-$C_6$ cycloalkenyl, a $C_6$-$C_8$ saturated bicyclic carbocycle, a $C_6$-$C_8$ partially unsaturated bicyclic carbocycle, phenyl, phenyl($C_1$-$C_3$)alkyl, pyridinyl, thiophenyl, thiazolyl, oxazolyl and pyrazolyl wherein the alkyl, cycloalkyl, alkenyl, cycloalkenyl and carbocycle may be optionally substituted with 1 to 3 substituents independently selected from fluoro, chloro, cyano, methyl, methoxy, methylthio, cyclopropyl and cyclobutyl, and wherein the phenyl, pyridinyl, thiophenyl, thiazolyl, oxazolyl and pyrazolyl may be optionally substituted with 1 to 3 of substituents independently selected from fluoro, chloro, cyano, methyl and cyclopropyl.

Even more preferably $R_7$ is $C_3$-$C_5$ alkyl, $C_3$-$C_7$ cycloalkyl, $C_3$-$C_4$ alkenyl, a $C_6$-$C_8$ saturated bicyclic carbocycle, phenyl, phenyl($C_1$-$C_2$)alkyl or pyridyl, wherein the alkyl, cycloalkyl, alkenyl and carbocycle may be optionally substituted with 1 to 3 substituents independently selected from fluoro and methyl or 1 or 2 substituents independently selected from cyclopropyl and cyclobutyl, and wherein the phenyl and pyridyl may be optionally substituted with 1 to 2 substituents independently selected from fluoro, chloro and methyl.

Most preferably $R_7$ is $C_3$-$C_5$ alkyl, cyclopropyl, cyclobutyl, cyclopentyl, cyclohexyl, cycloheptyl, $C_3$-$C_4$ alkenyl, phenyl or phenyl-$CH_2$—, wherein the alkyl, cyclopropyl, cyclobutyl, cyclopentyl, cyclohexyl, cycloheptyl and alkenyl may be optionally substituted with 1 to 3 fluoro substituents or 1 or 2 methyl substituents, and wherein the phenyl may be optionally substituted with 1 or 2 substituents independently selected from fluoro, chloro and methyl.

Embodiments according to the invention are provided as set out below.

Embodiment 1 provides compounds of formula (I), or a salt or N-oxide thereof, as defined above.

Embodiment 2 provides compounds according to embodiment 1, or a salt or N-oxide thereof, wherein $R_1$ is hydrogen, fluoro, chloro, bromo or methyl.

Embodiment 3 provides compounds according to embodiment 1 or 2, or a salt or N-oxide thereof, wherein $R_2$ is hydrogen, methyl, chloro or fluoro.

Embodiment 4 provides compounds according to any one of embodiments 1, 2 or 3, or a salt or N-oxide thereof, wherein $R_3$ and $R_4$ are each independently selected from hydrogen, chloro and methyl.

Embodiment 5 provides compounds according to any one of embodiments 1, 2, 3 or 4, or a salt or N-oxide thereof, wherein $R_5$ is $C_1$-$C_4$ alkyl, $C_1$-$C_2$ haloakyl, $C_2$-$C_4$ alkenyl or $C_3$-$C_6$ cycloalkyl, wherein the alkyl, alkenyl and cycloalkyl may be optionally substituted with 1 to 3 substituents independently selected from fluoro, cyano, methyl, methoxy and methylthio.

Embodiment 6 provides compounds according to any one of embodiments 1, 2, 3, 4, or 5, or a salt or N-oxide thereof, wherein $R_6$ is hydrogen or $C_1$-$C_3$ alkyl.

Embodiment 7 provides compounds according to any one of embodiments 1, 2, 3, 4, 5, or 6, or a salt or N-oxide thereof, wherein $R_7$ is $C_1$-$C_5$ alkyl, $C_3$-$C_7$ cycloalkyl, $C_3$-$C_5$ alkenyl, $C_3$-$C_6$ cycloalkenyl, $C_3$-$C_5$ alkynyl, a $C_5$-$C_{10}$ saturated bicyclic carbocycle, a $C_5$-$C_{10}$ partially unsaturated bicyclic carbocycle, phenyl, phenyl($C_1$-$C_3$)alkyl, oxetanyl, tetrahydrofuranyl, tetrahydropyranyl, pyridinyl, thiophenyl, thiazolyl, oxazolyl or pyrazolyl, wherein the alkyl, cycloalkyl, alkenyl, cycloalkenyl, carbocycle and alkynyl may be optionally substituted with one or more substituents independently selected from fluoro, chloro, cyano, methyl, methoxy, methylthio; $C_1$-$C_2$ fluoroalkoxy, $C_1$-$C_2$ fluoroalkylthio, cyclopropyl and cyclobutyl, and wherein the phenyl, oxetanyl, tetrahydrofuranyl, tetrahydropyranyl, pyridinyl, thiophenyl, thiazolyl, oxazolyl and pyrazolyl may be optionally substituted with one or more substituents independently selected from fluoro, chloro, cyano, methyl, methoxy, methylthio; $C_1$-$C_2$ fluoroalkoxy, $C_1$-$C_2$ fluoroalkylthio, cyclopropyl and cyclobutyl.

Embodiment 8 provides compounds according to any one of embodiments 1, 2, 3, 4, 5, 6, or 7, or a salt or N-oxide thereof, wherein $R_1$ is fluoro, chloro or methyl.

Embodiment 9 provides compounds according to any one of embodiments 1, 2, 3, 4, 5, 6, 7, or 8, or a salt or N-oxide thereof, wherein $R_2$ is hydrogen or fluoro.

Embodiment 10 provides compounds according to any one of embodiments 1, 2, 3, 4, 5, 6, 7, 8, or 9, or a salt or N-oxide thereof, wherein $R_3$ and $R_4$ are each independently selected from hydrogen and methyl.

Embodiment 11 provides compounds according to any one of embodiments 1, 2, 3, 4, 5, 6, 7, 8, 9 or 10, or a salt or N-oxide thereof, wherein $R_5$ is $C_1$-$C_4$ alkyl, $C_1$-haloakyl, $C_2$-$C_4$ alkenyl or $C_3$-$C_4$ cycloalkyl, wherein the alkyl, alkenyl and cycloalkyl may be optionally substituted with 1 to 3 substituents independently selected from fluoro, cyano and methyl.

Embodiment 12 provides compounds according to any one of embodiments 1, 2, 3, 4, 5, 6, 7, 8, 9, 10 or 11, or a salt or N-oxide thereof, wherein R$_6$ is hydrogen, methyl or ethyl.

Embodiment 13 provides compounds according to any one of embodiments 1, 2, 3, 4, 5, 6, 7, 8, 9, 10, 11 or 12, or a salt or N-oxide thereof, wherein R$_7$ is C$_1$-C$_5$ alkyl, C$_3$-C$_7$ cycloalkyl, C$_3$-C$_4$ alkenyl, C$_3$-C$_6$ cycloalkenyl, a C$_6$-C$_8$ saturated bicyclic carbocycle, a C$_6$-C$_8$ partially unsaturated bicyclic carbocycle, phenyl, phenyl(C$_1$-C$_3$)alkyl, pyridinyl, thiophenyl, thiazolyl, oxazolyl and pyrazolyl wherein the alkyl, cycloalkyl, alkenyl, cycloalkenyl and carbocycle may be optionally substituted with 1 to 3 substituents independently selected from fluoro, chloro, cyano, methyl, methoxy, methylthio, cyclopropyl and cyclobutyl, and wherein the phenyl, pyridinyl, thiophenyl, thiazolyl, oxazolyl and pyrazolyl may be optionally substituted with 1 to 3 of substituents independently selected from fluoro, chloro, cyano, methyl and cyclopropyl.

Embodiment 14 provides compounds according to any one of embodiments 1, 2, 3, 4, 5, 6, 7, 8, 9, 10, 11, 12 or 13, or a salt or N-oxide thereof, wherein R$_7$ is C$_1$-C$_4$ alkyl, C$_3$-C$_4$ cycloalkyl, or C$_2$-C$_4$ alkenyl, wherein R$_1$ is fluoro or methyl.

Embodiment 15 provides compounds according to any one of embodiments 1, 2, 3, 4, 5, 6, 7, 8, 9, 10, 11, 12, 13 or 14, or a salt or N-oxide thereof, wherein R$_2$ is hydrogen.

Embodiment 16 provides compounds according to any one of embodiments 1, 2, 3, 4, 5, 6, 7, 8, 9, 10, 11, 12, 13, 14 or 15, or a salt or N-oxide thereof, wherein R$_3$ is methyl and R$_4$ is hydrogen; or R$_3$ is hydrogen and R$_4$ is methyl; or R$_3$ is hydrogen and R$_4$ is hydrogen.

Embodiment 17 provides compounds according to any one of embodiments 1, 2, 3, 4, 5, 6, 7, 8, 9, 10, 11, 12, 13, 14, 15 or 16, or a salt or N-oxide thereof, wherein R$_5$ is C$_1$-C$_4$ alkyl, trifluoromethyl, C$_2$-C$_4$ alkenyl or C$_3$-C$_4$ cycloalkyl, wherein the alkyl, alkenyl and cycloalkyl may be optionally substituted with 1 to 3 fluorine atoms or a methyl.

Embodiment 18 provides compounds according to any one of embodiments 1, 2, 3, 4, 5, 6, 7, 8, 9, 10, 11, 12, 13, 14, 15, 16 or 17, or a salt or N-oxide thereof, wherein R$_6$ is methyl.

Embodiment 19 provides compounds according to any one of embodiments 1, 2, 3, 4, 5, 6, 7, 8, 9, 10, 11, 12, 13, 14, 15, 16, 17 or 18, or a salt or N-oxide thereof, wherein R$_7$ is C$_3$-C$_5$ alkyl, C$_3$-C$_7$ cycloalkyl, C$_3$-C$_4$ alkenyl, a C$_6$-C$_8$ saturated bicyclic carbocycle, phenyl, phenyl(C$_1$-C$_2$)alkyl or pyridyl, wherein the alkyl, cycloalkyl, alkenyl and carbocycle may be optionally substituted with 1 to 3 substituents independently selected from fluoro and methyl or 1 or 2 substituents independently selected from cyclopropyl and cyclobutyl, and wherein the phenyl and pyridyl may be optionally substituted with 1 to 2 substituents independently selected from fluoro, chloro and methyl.

Embodiment 20 provides compounds according to any one of embodiments 1, 2, 3, 4, 5, 6, 7, 8, 9, 10, 11, 12, 13, 14, 15, 16, 17, 18 or 19, or a salt or N-oxide thereof, wherein R$_3$ and R$_4$ are both hydrogen.

Embodiment 21 provides compounds according to any one of embodiments 1, 2, 3, 4, 5, 6, 7, 8, 9, 10, 11, 12, 13, 14, 15, 16, 17, 18, 19 or 20, or a salt or N-oxide thereof, wherein.

Embodiment 22 provides compounds according to any one of embodiments 1, 2, 3, 4, 5, 6, 7, 8, 9, 10, 11, 12, 13, 14, 15, 16, 17, 18, 19, 20 or 21, or a salt or N-oxide thereof, wherein R$_5$ is ethyl, n-propyl, iso-propyl, n-butyl, sec-butyl, iso-butyl, tert-butyl or trifluoromethyl.

Embodiment 23 provides compounds according to any one of embodiments 1, 2, 3, 4, 5, 6, 7, 8, 9, 10, 11, 12, 13, 14, 15, 16, 17, 18, 19, 20, 21 or 22, or a salt or N-oxide thereof, wherein R$_7$ is C$_3$-C$_5$ alkyl, cyclopropyl, cyclobutyl, cyclopentyl, cyclohexyl, cycloheptyl, C$_3$-C$_4$ alkenyl, phenyl or phenyl-CH$_2$—, wherein the alkyl, cyclopropyl, cyclobutyl, cyclopentyl, cyclohexyl, cycloheptyl and alkenyl may be optionally substituted with 1 to 3 fluoro substituents or 1 or 2 methyl substituents, and wherein the phenyl may be optionally substituted with 1 or 2 substituents independently selected from fluoro, chloro and methyl.

Embodiment 24 provides compounds according to any one of embodiments 1, 2, 3, 4, 5, 6, 7, 8, 9, 10, 11, 12, 13, 14, 15, 16, 17, 18, 19, 20, 21, 22 or 23, or a salt or N-oxide thereof, wherein X is O.

Embodiment 25 provides compounds according to any one of embodiments 1, 2, 3, 4, 5, 6, 7, 8, 9, 10, 11, 12, 13, 14, 15, 16, 17, 18, 19, 20, 21, 22 or 23, or a salt or N-oxide thereof, wherein X is S.

One group of compounds according to the invention are those of formula (I'):

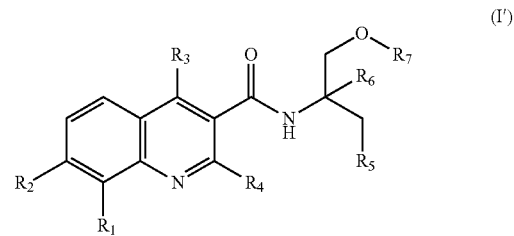

wherein R$_1$, R$_2$, R$_3$, R$_4$, R$_5$, R$_6$ and R$_7$ are as defined for compounds of formula (I), or a salt or N-oxide thereof. Preferred definitions of R$_1$, R$_2$, R$_3$, R$_4$, R$_5$, R$_6$ and R$_7$ are as defined for compounds of formula (I).

One group of compounds according to the invention are those of formula (I"):

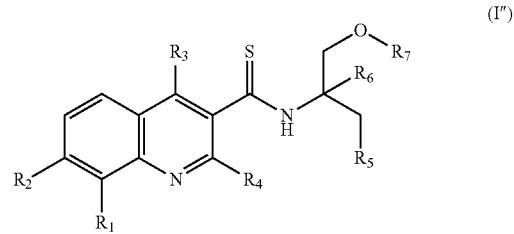

wherein R$_1$, R$_2$, R$_3$, R$_4$, R$_5$, R$_6$ and R$_7$ are as defined for compounds of formula (I), or a salt or N-oxide thereof. Preferred definitions of R$_1$, R$_2$, R$_3$, R$_4$, R$_5$, R$_6$ and R$_7$ are as defined for compounds of formula (I).

A preferred group of compounds according to the invention are those of formula (I-1) which are compounds of formula (I) wherein X is O or S; R$_1$ is hydrogen, fluoro, chloro, bromo or methyl; R$_2$ is hydrogen, methyl, chloro or fluoro; R$_3$ and R$_4$ are each independently selected from hydrogen, chloro and methyl; R$_5$ is C$_1$-C$_4$ alkyl, C$_1$-C$_2$ haloalkyl, C$_2$-C$_4$ alkenyl or C$_3$-C$_6$ cycloalkyl, wherein the alkyl, alkenyl and cycloalkyl may be optionally substituted with 1 to 3 substituents independently selected from fluoro, cyano, methyl, methoxy and methylthio; R$_6$ is hydrogen or C$_1$-C$_3$ alkyl; R$_7$ is C$_1$-C$_5$ alkyl, C$_3$-C$_7$ cycloalkyl, C$_3$-C$_5$ alkenyl, $C_3$-$C_6$ cycloalkenyl, $C_3$-$C_5$ alkynyl, a $C_5$-$C_{10}$ saturated bicyclic carbocycle, a $C_5$-$C_{10}$ partially unsaturated bicyclic carbocycle, phenyl, phenyl($C_1$-$C_3$)alkyl, oxetanyl, tetrahydrofuranyl, tetrahydropyranyl, pyridinyl, thiophenyl, thiazolyl, oxazolyl or pyrazolyl, wherein the alkyl, cycloalkyl, alkenyl, cycloalkenyl, carbocycle and alkynyl may be optionally substituted with one or more substituents independently selected from fluoro, chloro, cyano, methyl, methoxy, methylthio; $C_1$-$C_2$ fluoroalkoxy, $C_1$-$C_2$ fluoroalkylthio, cyclopropyl and cyclobutyl, and wherein the phenyl, oxetanyl, tetrahydrofuranyl, tetrahydropyranyl, pyridinyl, thiophenyl, thiazolyl, oxazolyl and pyrazolyl may be optionally substituted with one or more substituents independently selected from fluoro, chloro, cyano, methyl, methoxy, methylthio; $C_1$-$C_2$ fluoroalkoxy, $C_1$-$C_2$ fluoroalkylthio, cyclopropyl and cyclobutyl; or a salt or N-oxide thereof.

One group of compounds according to this embodiment are compounds of formula (I-1a) which are compounds of formula (I-1) wherein X is O.

Another group of compounds according to this embodiment are compounds of formula (I-1b) which are compounds of formula (I-1) wherein X is S.

A further preferred group of compounds according to the invention are those of formula (I-2) which are compounds of formula (I) wherein X is O or S; $R_1$ is fluoro, chloro or methyl; $R_2$ is hydrogen or fluoro; $R_3$ and $R_4$ are each independently selected from hydrogen and methyl; $R_5$ is $C_1$-$C_4$ alkyl, $C_1$-haloakyl, $C_2$-$C_4$ alkenyl or $C_3$-$C_4$ cycloalkyl, wherein the alkyl, alkenyl and cycloalkyl may be optionally substituted with 1 to 3 substituents independently selected from fluoro, cyano and methyl; $R_6$ is hydrogen, methyl or ethyl; $R_7$ is $C_1$-$C_5$ alkyl, $C_3$-$C_7$ cycloalkyl, $C_3$-$C_4$ alkenyl, $C_3$-$C_6$ cycloalkenyl, a $C_6$-$C_8$ saturated bicyclic carbocycle, a $C_6$-$C_8$ partially unsaturated bicyclic carbocycle, phenyl, phenyl($C_1$-$C_3$)alkyl, pyridinyl, thiophenyl, thiazolyl, oxazolyl and pyrazolyl wherein the alkyl, cycloalkyl, alkenyl, cycloalkenyl and carbocycle may be optionally substituted with 1 to 3 substituents independently selected from fluoro, chloro, cyano, methyl, methoxy, methylthio, cyclopropyl and cyclobutyl, and wherein the phenyl, pyridinyl, thiophenyl, thiazolyl, oxazolyl and pyrazolyl may be optionally substituted with 1 to 3 of substituents independently selected from fluoro, chloro, cyano, methyl and cyclopropyl; or a salt or N-oxide thereof.

One group of compounds according to this embodiment are compounds of formula (I-2a) which are compounds of formula (I-2) wherein X is O.

Another group of compounds according to this embodiment are compounds of formula (I-2b) which are compounds of formula (I-2) wherein X is S.

A further preferred group of compounds according to the invention are those of formula (I-3) which are compounds of formula (I) wherein X is O or S; $R_1$ is fluoro or methyl; $R_2$ is hydrogen; $R_3$ is methyl and $R_4$ is hydrogen; or $R_3$ is hydrogen and $R_4$ is methyl; or $R_3$ is hydrogen and $R_4$ is hydrogen; $R_5$ is $C_1$-$C_4$ alkyl, trifluoromethyl, $C_2$-$C_4$ alkenyl or $C_3$-$C_4$ cycloalkyl, wherein the alkyl, alkenyl and cycloalkyl may be optionally substituted with 1 to 3 fluorine atoms or a methyl; $R_6$ is methyl; $R_7$ is $C_3$-$C_5$ alkyl, $C_3$-$C_7$ cycloalkyl, $C_3$-$C_4$ alkenyl, a $C_6$-$C_8$ saturated bicyclic carbocycle, phenyl, phenyl($C_1$-$C_2$)alkyl or pyridyl, wherein the alkyl, cycloalkyl, alkenyl and carbocycle may be optionally substituted with 1 to 3 substituents independently selected from fluoro and methyl or 1 or 2 substituents independently selected from cyclopropyl and cyclobutyl, and wherein the phenyl and pyridyl may be optionally substituted with 1 to 2 substituents independently selected from fluoro, chloro and methyl; or a salt or N-oxide thereof.

One group of compounds according to this embodiment are compounds of formula (I-3a) which are compounds of formula (I-3) wherein X is O.

Another group of compounds according to this embodiment are compounds of formula (I-3b) which are compounds of formula (I-3) wherein X is S.

Compounds according to the invention may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile, improved physico-chemical properties, or increased biodegradability).

Specific examples of compounds of formula (I) are illustrated in the Tables A1 to A8 below:

Table A1 provides 192 compounds of formula (I-a)

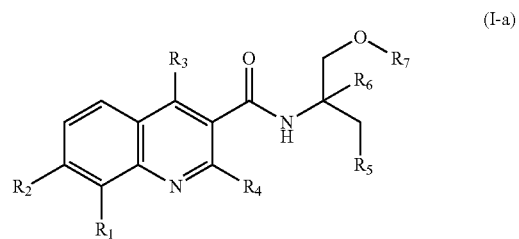

(I-a)

wherein $R_1$, $R_2$, $R_3$ and $R_4$ are all H
and wherein the values of $R_5$, $R_6$ and $R_7$ are as defined in Table Z below:

TABLE Z

| Entry | $R_5$ | $R_6$ | $R_7$ |
|---|---|---|---|
| 1 | $CH(CH_3)_2$ | H | phenyl |
| 2 | $C(CH_3)=CH_2$ | H | phenyl |
| 3 | $C(F)=CH_2$ | H | phenyl |
| 4 | $C(CH3)3$ | H | phenyl |
| 5 | $CF_3$ | H | phenyl |
| 6 | $CH=CH_2$ | H | phenyl |
| 7 | cyclopropyl | H | phenyl |
| 8 | 1-methylcyclopropyl | H | phenyl |
| 9 | 1-fluorocyclopropyl | H | phenyl |
| 10 | 1-cyanocyclopropyl | H | phenyl |
| 11 | $CF(CH_3)_2$ | H | phenyl |
| 12 | $CF_2CH_3$ | H | phenyl |
| 13 | $CH(CH_3)_2$ | H | 4-F-phenyl |
| 14 | $C(CH_3)=CH_2$ | H | 4-F-phenyl |
| 15 | $C(F)=CH_2$ | H | 4-F-phenyl |
| 16 | $C(CH_3)_3$ | H | 4-F-phenyl |
| 17 | $CF_3$ | H | 4-F-phenyl |
| 18 | $CH=CH_2$ | H | 4-F-phenyl |
| 19 | cyclopropyl | H | 4-F-phenyl |
| 20 | 1-methylcyclopropyl | H | 4-F-phenyl |
| 21 | 1-fluorocyclopropyl | H | 4-F-phenyl |
| 22 | 1-cyanocyclopropyl | H | 4-F-phenyl |
| 23 | $CF(CH_3)_2$ | H | 4-F-phenyl |
| 24 | $CF_2CH_3$ | H | 4-F-phenyl |
| 25 | $CH(CH_3)_2$ | H | cyclohexyl |
| 26 | $C(CH_3)=CH_2$ | H | cyclohexyl |
| 27 | $C(F)=CH_2$ | H | cyclohexyl |
| 28 | $C(CH_3)_3$ | H | cyclohexyl |
| 29 | $CF_3$ | H | cyclohexyl |
| 30 | $CH=CH_2$ | H | cyclohexyl |
| 31 | cyclopropyl | H | cyclohexyl |
| 32 | 1-methylcyclopropyl | H | cyclohexyl |
| 33 | 1-fluorocyclopropyl | H | cyclohexyl |
| 34 | 1-cyanocyclopropyl | H | cyclohexyl |
| 35 | $CF(CH_3)_2$ | H | cyclohexyl |
| 36 | $CF_2CH_3$ | H | cyclohexyl |
| 37 | $CH(CH_3)_2$ | H | cyclopentyl |

TABLE Z-continued

| Entry | R$_5$ | R$_6$ | R$_7$ |
|---|---|---|---|
| 38 | C(CH$_3$)=CH$_2$ | H | cyclopentyl |
| 39 | C(F)=CH$_2$ | H | cyclopentyl |
| 40 | C(CH$_3$)$_3$ | H | cyclopentyl |
| 41 | CF$_3$ | H | cyclopentyl |
| 42 | CH=CH$_2$ | H | cyclopentyl |
| 43 | cyclopropyl | H | cyclopentyl |
| 45 | 1-methylcyclopropyl | H | cyclopentyl |
| 46 | 1-fluorocyclopropyl | H | cyclopentyl |
| 47 | 1-cyanocyclopropyl | H | cyclopentyl |
| 48 | CF$_2$CH$_3$ | H | cyclopentyl |
| 49 | CH(CH$_3$)$_2$ | H | C(CH$_3$)$_3$ |
| 50 | C(CH$_3$)=CH$_2$ | H | C(CH$_3$)$_3$ |
| 51 | C(F)=CH$_2$ | H | C(CH$_3$)$_3$ |
| 52 | C(CH$_3$)$_3$ | H | C(CH$_3$)$_3$ |
| 53 | CF$_3$ | H | C(CH$_3$)$_3$ |
| 54 | CH=CH$_2$ | H | C(CH$_3$)$_3$ |
| 55 | cyclopropyl | H | C(CH$_3$)$_3$ |
| 56 | 1-methylcyclopropyl | H | C(CH$_3$)$_3$ |
| 57 | 1-fluorocyclopropyl | H | C(CH$_3$)$_3$ |
| 58 | 1-cyanocyclopropyl | H | C(CH$_3$)$_3$ |
| 59 | CF(CH$_3$)$_2$ | H | C(CH$_3$)$_3$ |
| 60 | CF$_2$CH$_3$ | H | C(CH$_3$)$_3$ |
| 61 | CH(CH$_3$)$_2$ | H | 1-methyl cylopentyl |
| 62 | C(CH$_3$)=CH$_2$ | H | 1-methyl cylopentyl |
| 63 | C(F)=CH$_2$ | H | 1-methyl cylopentyl |
| 64 | C(CH$_3$)$_3$ | H | 1-methyl cylopentyl |
| 65 | CF$_3$ | H | 1-methyl cylopentyl |
| 66 | CH=CH$_2$ | H | 1-methyl cylopentyl |
| 67 | cyclopropyl | H | 1-methyl cylopentyl |
| 68 | 1-methylcyclopropyl | H | 1-methyl cylopentyl |
| 69 | 1-fluorocyclopropyl | H | 1-methyl cylopentyl |
| 70 | 1-cyanocyclopropyl | H | 1-methyl cylopentyl |
| 71 | CF(CH$_3$)$_2$ | H | 1-methyl cylopentyl |
| 72 | CF$_2$CH$_3$ | H | 1-methyl cylopentyl |
| 73 | CH(CH$_3$)$_2$ | H | 1-methyl cylohexyl |
| 74 | C(CH$_3$)=CH$_2$ | H | 1-methyl cylohexyl |
| 75 | C(F)=CH$_2$ | H | 1-methyl cylohexyl |
| 76 | C(CH$_3$)$_3$ | H | 1-methyl cylohexyl |
| 77 | CF$_3$ | H | 1-methyl cylohexyl |
| 78 | CH=CH$_2$ | H | 1-methyl cylohexyl |
| 79 | cyclopropyl | H | 1-methyl cylohexyl |
| 80 | 1-methylcyclopropyl | H | 1-methyl cylohexyl |
| 81 | 1-fluorocyclopropyl | H | 1-methyl cylohexyl |
| 82 | 1-cyanocyclopropyl | H | 1-methyl cylohexyl |
| 83 | CF(CH$_3$)$_2$ | H | 1-methyl cylohexyl |
| 84 | CF$_2$CH$_3$ | H | 1-methyl cylohexyl |
| 85 | CH(CH$_3$)$_2$ | CH$_3$ | phenyl |
| 86 | C(CH$_3$)=CH$_2$ | CH$_3$ | phenyl |
| 87 | C(F)=CH$_2$ | CH$_3$ | phenyl |
| 88 | C(CH$_3$)$_3$ | CH$_3$ | phenyl |
| 89 | CF$_3$ | CH$_3$ | phenyl |
| 90 | CH=CH$_2$ | CH$_3$ | phenyl |
| 91 | cyclopropyl | CH$_3$ | phenyl |
| 92 | 1-methylcyclopropyl | CH$_3$ | phenyl |
| 93 | 1-fluorocyclopropyl | CH$_3$ | phenyl |
| 94 | 1-cyanocyclopropyl | CH$_3$ | phenyl |
| 95 | CF(CH$_3$)$_2$ | CH$_3$ | phenyl |
| 96 | CF$_2$CH$_3$ | CH$_3$ | phenyl |
| 97 | CH(CH$_3$)$_2$ | CH$_3$ | 4-F-phenyl |
| 98 | C(CH$_3$)=CH$_2$ | CH$_3$ | 4-F-phenyl |
| 99 | C(F)=CH$_2$ | CH$_3$ | 4-F-phenyl |
| 100 | C(CH$_3$)$_3$ | CH$_3$ | 4-F-phenyl |
| 101 | CF$_3$ | CH$_3$ | 4-F-phenyl |
| 102 | CH=CH$_2$ | CH$_3$ | 4-F-phenyl |
| 103 | cyclopropyl | CH$_3$ | 4-F-phenyl |
| 104 | 1-methylcyclopropyl | CH$_3$ | 4-F-phenyl |
| 105 | 1-fluorocyclopropyl | CH$_3$ | 4-F-phenyl |
| 106 | 1-cyanocyclopropyl | CH$_3$ | 4-F-phenyl |
| 107 | CF(CH$_3$)$_2$ | CH$_3$ | 4-F-phenyl |
| 108 | CF$_2$CH$_3$ | CH$_3$ | 4-F-phenyl |
| 109 | CH(CH$_3$)$_2$ | CH$_3$ | cyclohexyl |
| 110 | C(CH$_3$)=CH$_2$ | CH$_3$ | cyclohexyl |
| 111 | C(F)=CH$_2$ | CH$_3$ | cyclohexyl |
| 112 | C(CH$_3$)$_3$ | CH$_3$ | cyclohexyl |
| 113 | CF$_3$ | CH$_3$ | cyclohexyl |
| 114 | CH=CH$_2$ | CH$_3$ | cyclohexyl |
| 115 | cyclopropyl | CH$_3$ | cyclohexyl |
| 116 | 1-methylcyclopropyl | CH$_3$ | cyclohexyl |
| 117 | 1-fluorocyclopropyl | CH$_3$ | cyclohexyl |
| 118 | 1-cyanocyclopropyl | CH$_3$ | cyclohexyl |
| 119 | CF(CH$_3$)$_2$ | CH$_3$ | cyclohexyl |
| 120 | CF$_2$CH$_3$ | CH$_3$ | cyclohexyl |
| 121 | CH(CH$_3$)$_2$ | CH$_3$ | cyclopentyl |
| 122 | C(CH$_3$)=CH$_2$ | CH$_3$ | cyclopentyl |
| 123 | C(F)=CH$_2$ | CH$_3$ | cyclopentyl |
| 124 | C(CH$_3$)$_3$ | CH$_3$ | cyclopentyl |
| 125 | CF$_3$ | CH$_3$ | cyclopentyl |
| 126 | CH=CH$_2$ | CH$_3$ | cyclopentyl |
| 127 | cyclopropyl | CH$_3$ | cyclopentyl |
| 128 | 1-methylcyclopropyl | CH$_3$ | cyclopentyl |
| 129 | 1-fluorocyclopropyl | CH$_3$ | cyclopentyl |
| 130 | 1-cyanocyclopropyl | CH$_3$ | cyclopentyl |
| 131 | CF(CH$_3$)$_2$ | CH$_3$ | cyclopentyl |
| 132 | CF$_2$CH$_3$ | CH$_3$ | cyclopentyl |
| 133 | CH(CH$_3$)$_2$ | CH$_3$ | C(CH$_3$)$_3$ |
| 134 | C(CH$_3$)=CH$_2$ | CH$_3$ | C(CH$_3$)$_3$ |
| 135 | C(F)=CH$_2$ | CH$_3$ | C(CH$_3$)$_3$ |
| 136 | C(CH$_3$)$_3$ | CH$_3$ | C(CH$_3$)$_3$ |
| 137 | CF$_3$ | CH$_3$ | C(CH$_3$)$_3$ |
| 138 | CH=CH$_2$ | CH$_3$ | C(CH$_3$)$_3$ |
| 139 | cyclopropyl | CH$_3$ | C(CH$_3$)$_3$ |
| 140 | 1-methylcyclopropyl | CH$_3$ | C(CH$_3$)$_3$ |
| 141 | 1-fluorocyclopropyl | CH$_3$ | C(CH$_3$)$_3$ |
| 142 | 1-cyanocyclopropyl | CH$_3$ | C(CH$_3$)$_3$ |
| 143 | CF(CH$_3$)$_2$ | CH$_3$ | C(CH$_3$)$_3$ |
| 144 | CF$_2$CH$_3$ | CH$_3$ | C(CH$_3$)$_3$ |
| 145 | CH(CH$_3$)$_2$ | CH$_3$ | 1-methyl cylopentyl |
| 146 | C(CH$_3$)=CH$_2$ | CH$_3$ | 1-methyl cylopentyl |
| 147 | C(F)=CH$_2$ | CH$_3$ | 1-methyl cylopentyl |
| 148 | C(CH$_3$)$_3$ | CH$_3$ | 1-methyl cylopentyl |
| 149 | CF$_3$ | CH$_3$ | 1-methyl cylopentyl |
| 150 | CH=CH$_2$ | CH$_3$ | 1-methyl cylopentyl |
| 151 | cyclopropyl | CH$_3$ | 1-methyl cylopentyl |
| 152 | 1-methylcyclopropyl | CH$_3$ | 1-methyl cylopentyl |
| 153 | 1-fluorocyclopropyl | CH$_3$ | 1-methyl cylopentyl |
| 154 | 1-cyanocyclopropyl | CH$_3$ | 1-methyl cylopentyl |
| 155 | CF(CH$_3$)$_2$ | CH$_3$ | 1-methyl cylopentyl |
| 156 | CF$_2$CH$_3$ | CH$_3$ | 1-methyl cylopentyl |
| 157 | CH(CH$_3$)$_2$ | CH$_3$ | 1-methyl cylohexyl |
| 158 | C(CH$_3$)=CH$_2$ | CH$_3$ | 1-methyl cylohexyl |
| 159 | C(F)=CH$_2$ | CH$_3$ | 1-methyl cylohexyl |
| 160 | C(CH$_3$)$_3$ | CH$_3$ | 1-methyl cylohexyl |
| 161 | CF$_3$ | CH$_3$ | 1-methyl cylohexyl |
| 162 | CH=CH$_2$ | CH$_3$ | 1-methyl cylohexyl |
| 163 | cyclopropyl | CH$_3$ | 1-methyl cylohexyl |
| 164 | 1-methylcyclopropyl | CH$_3$ | 1-methyl cylohexyl |
| 165 | 1-fluorocyclopropyl | CH$_3$ | 1-methyl cylohexyl |
| 166 | 1-cyanocyclopropyl | CH$_3$ | 1-methyl cylohexyl |
| 167 | CF(CH$_3$)$_2$ | CH$_3$ | 1-methyl cylohexyl |
| 168 | CF$_2$CH$_3$ | CH$_3$ | 1-methyl cylohexyl |
| 169 | CH(CH$_3$)$_2$ | CH$_3$ | cyclobutyl |
| 170 | C(CH$_3$)=CH$_2$ | CH$_3$ | cyclobutyl |
| 171 | C(F)=CH$_2$ | CH$_3$ | cyclobutyl |
| 172 | C(CH$_3$)$_3$ | CH$_3$ | cyclobutyl |
| 173 | CF$_3$ | CH$_3$ | cyclobutyl |
| 174 | CH=CH$_2$ | CH$_3$ | cyclobutyl |
| 175 | cyclopropyl | CH$_3$ | cyclobutyl |
| 176 | 1-methylcyclopropyl | CH$_3$ | cyclobutyl |
| 177 | 1-fluorocyclopropyl | CH$_3$ | cyclobutyl |
| 178 | 1-cyanocyclopropyl | CH$_3$ | cyclobutyl |
| 179 | CF(CH$_3$)$_2$ | CH$_3$ | cyclobutyl |
| 180 | CF$_2$CH$_3$ | CH$_3$ | cyclobutyl |
| 181 | CH(CH$_3$)$_2$ | CH$_3$ | 1-methyl cyclobutyl |
| 182 | C(CH$_3$)=CH$_2$ | CH$_3$ | 1-methyl cyclobutyl |
| 183 | C(F)=CH$_2$ | CH$_3$ | 1-methyl cyclobutyl |
| 184 | C(CH$_3$)$_3$ | CH$_3$ | 1-methyl cyclobutyl |
| 185 | CF$_3$ | CH$_3$ | 1-methyl cyclobutyl |
| 186 | CH=CH$_2$ | CH$_3$ | 1-methyl cyclobutyl |
| 187 | cyclopropyl | CH$_3$ | 1-methyl cyclobutyl |
| 188 | 1-methylcyclopropyl | CH$_3$ | 1-methyl cyclobutyl |
| 189 | 1-fluorocyclopropyl | CH$_3$ | 1-methyl cyclobutyl |
| 190 | 1-cyanocyclopropyl | CH$_3$ | 1-methyl cyclobutyl |
| 191 | CF(CH$_3$)$_2$ | CH$_3$ | 1-methyl cyclobutyl |
| 192 | CF$_2$CH$_3$ | CH$_3$ | 1-methyl cyclobutyl |

Table A2 provides 192 compounds of formula (I-a) wherein $R_1$ is $CH_3$ and $R_2$, $R_3$ and $R_4$ are all H and wherein the values of $R_5$, $R_6$ and $R_7$ are as defined in Table Z above.

Table A3 provides 192 compounds of formula (I-a) wherein $R_1$ is F and $R_2$, $R_3$ and $R_4$ are all H and wherein the values of $R_5$, $R_6$ and $R_7$ are as defined in Table Z above.

Table A4 provides 192 compounds of formula (I-a) wherein $R_1$ is Cl and $R_2$, $R_3$ and $R_4$ are all H and wherein the values of $R_5$, $R_6$ and $R_7$ are as defined in Table Z above.

Table A5 provides 192 compounds of formula (I-a) wherein $R_1$ is F, $R_2$ is F, $R_3$ and $R_4$ are both H and wherein the values of $R_5$, $R_6$ and $R_7$ are as defined in Table Z above.

Table A6 provides 192 compounds of formula (I-a) wherein $R_1$ is F, $R_2$ is H, $R_3$ is $CH_3$ and $R_4$ is H and wherein the values of $R_5$, $R_6$ and $R_7$ are as defined in Table Z above.

Table A7 provides 192 compounds of formula (I-a) wherein $R_1$ is F, $R_2$ is H, $R_3$ is H and $R_4$ is $CH_3$ and wherein the values of $R_5$, $R_6$ and $R_7$ are as defined in Table Z above. Table A8 provides 192 compounds of formula (I-b)

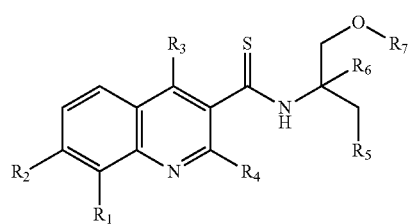

(I-b)

wherein $R_1$ is F, $R_2$, $R_3$ and $R_4$ are all H and wherein the values of $R_5$, $R_6$ and $R_7$ are as defined in Table Z above.

Compounds of the present invention can be made as shown in the following schemes, in which, unless otherwise stated, the definition of each variable is as defined above for a compound of formula (I).

A shown in scheme 1, compounds of general formula (I-a) wherein X is O can be prepared by the reaction of compounds of formula (II) with amines of formula (III).

Scheme 1

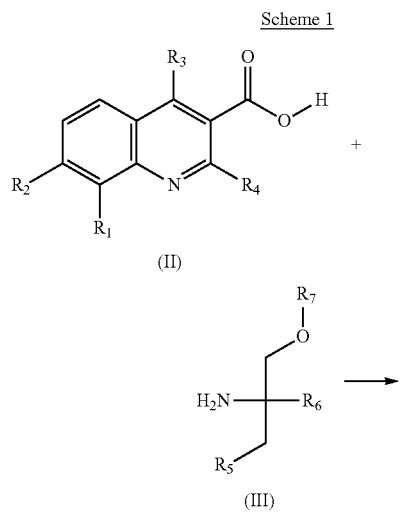

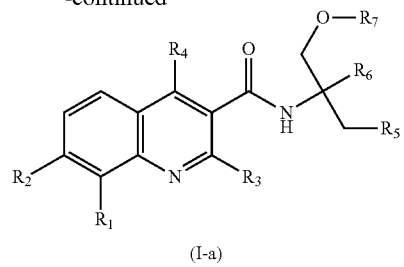

(I-a)

Among the various reported methods for this transformation, the most widely applied involve treatment of carboxylic acid (II) with an activating agent like thionyl chloride or an amide coupling reagent like dicyclohexylcarbodiimide in an inert organic solvent like tetrahydrofuran (THF) or dimethylformamide (DMF) and reaction with amine (III) in the presence of a catalyst like dimethylaminopyridine as described in *Chem. Soc. Rev.*, 2009, 606-631 or *Tetrahedron* 2005, 10827-10852.

Alternatively, compounds of general formula (I-a) wherein X is O can also be prepared by the reaction of compounds of formula (IV) with amines of formula (III), carbon monoxide, a base like triethylamine or potassium carbonate and a suitably supported transitional metal catalyst like palladium in an inert organic solvent like 1,4-dioxane at a temperature between 20° C. and 110° C. as described in *Org. Lett.*, 2014, 4296-4299 (and references therein) and shown in scheme 2.

Scheme 2

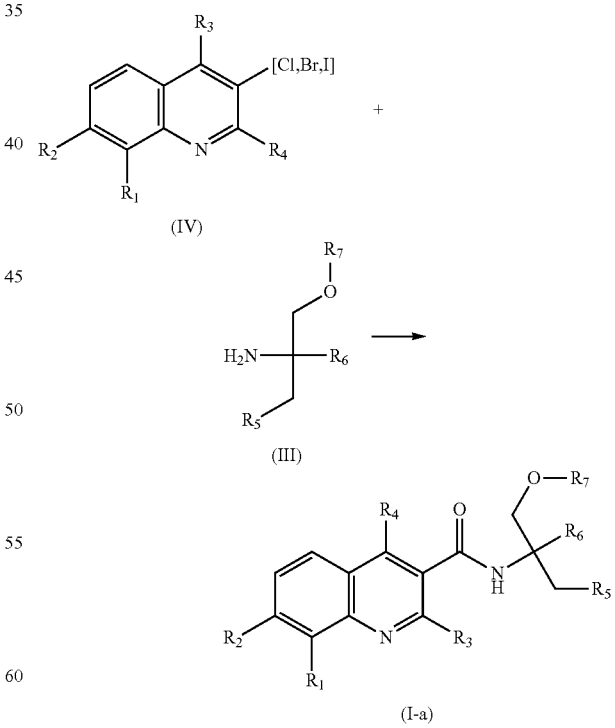

Alternatively, compounds of general formula (I-a) wherein X is O can also be prepared by the reaction of organometallic compounds of formula (VIa) with isocyanates of formula (IIIa) in an inert organic solvent like diethyl ether or THF at temperatures between −78° C. and +40° C. as described in *Angew. Chem. Int. Ed.* 2012, 9173-9175 and shown in scheme 3.

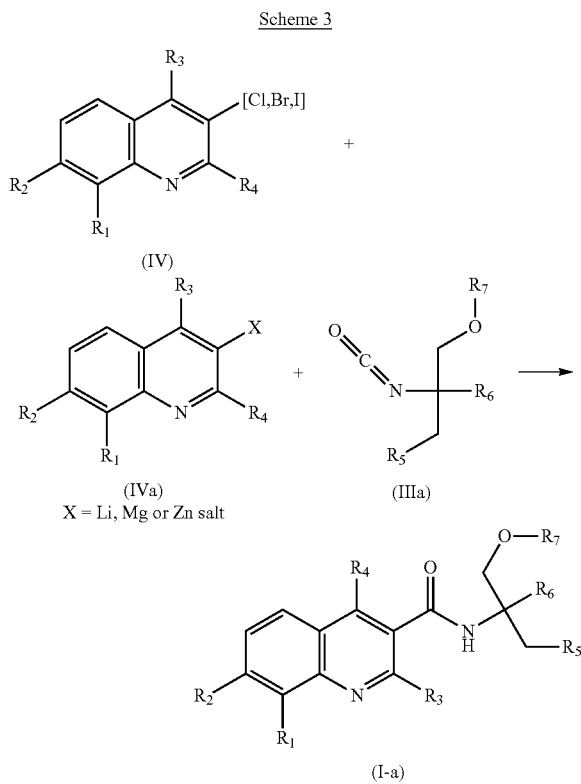

The preparation of organometallic compounds of formula (IVa) from compounds of formula (IV) by lithium-halogen exchange with an alkyl lithium reagent like s-butyl lithium, direct zinc insertion or magnesium-halogen exchange with tri n-butyl magnesate is known to a person skilled in the art, and is described in synthetic chemistry texts such as *March's Advanced Organic Chemistry*.

As shown in scheme 4, compounds of formula (III) and (IIIa) can be prepared from carboxylic acid derivatives of formula (Va) or (Vb).

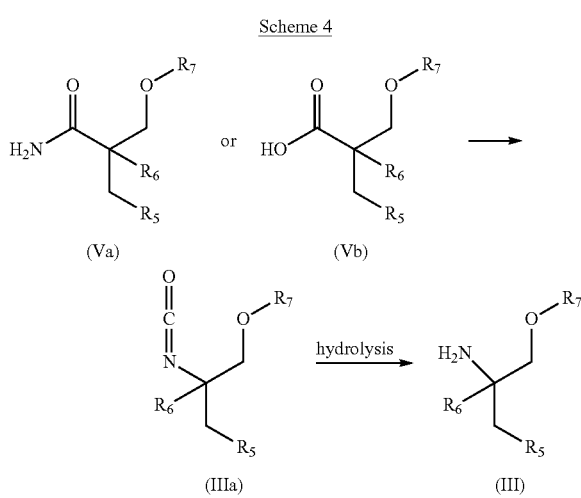

Among the various protocols reported for the transformation of carboxylic acid derivatives (Va) or (Vb) to isocyanate (IIIa), the following have found wide spread application:

1) Treatment of acid (Vb) with diphenylphosphoryl azide and an amine base like tributylamine in an inert organic solvent like toluene at temperatures between 50° C. and 120° C. to give isocyanate (IIIa) as described in *Aust. J. Chem.*, 1973, 1591-3.

2) Treatment of acid (Vb) with an activating agent like thionyl chloride or propylphosphonic anhydride in the presence of an azide source like sodium azide and an amine base like triethyl amine in an inert solvent like THF at temperatures between 20° C. and 100° C., followed by thermal rearrangement in an inert solvent such as toluene as described in Synthesis 2011, 1477-1483.

3) Treatment of carboxamides (Va) with an oxidizing agent such as bromine or diacetoxyiodobenzene and an acid such as para-toluenesulfonic acid or a base such as sodium hydroxide in a solvent like acetonitrile or dioxane at temperatures between 0° C. and 100° C. as described in *J. Org. Chem.* 1984, 4212-4216.

A person skilled in the art will appreciate that carboxylic acids of formula (Va) and (Vb) can be prepared from the corresponding esters. Similarly a person skilled in the art will appreciate that the alpha position of these esters can be functionalized by deprotonation with a strong base like lithium diisopropylamide in an inert solvent like THF at temperatures between −78° C. and 20° C. followed by reaction with an electrophilic reagent such as an alkyl halide as described in *March's Advanced Organic Chemistry*, Smith and March, 6$^{th}$ edition, Wiley, 2007. This reaction can be repeated and the introduced alkyl, alkenyl and alkynyl groups can be further functionalized by halogenation, cyclopropanation, oxidation or reduction to prepare acid derivatives of formula (Va) and (Vb) from commercially available esters.

As shown in scheme 5, amines of formula (III) can be prepared from compounds of formula (IIIc) by condensation with a sulfinamide (IIIe), where $R_9$ is $C_2$-$C_6$alkyl or phenyl and the phenyl group can be substituted with 1 to 3 groups independently selected from $C_1$-$C_4$alkyl and nitro, in the presence of a dehydrating agent like Ti(OEt)$_4$ to form sulfimines of formula (IIIb) which can then be treated with an organometallic reagent of formula (IIId), where X is lithium, an aluminum- or a magnesium-salt, in an inert solvent like THF at temperatures between −78° C. and +70° C., followed by an acidic hydrolysis of the sulfonamide; a sequence generally known to a person skilled in the art and also described in *Chem. Rev.* 2010, 3600-3740.

Alternatively, amines of formula (III) can be prepared from compounds of formula (IIIf) by a closely related sequence as described above and shown in scheme 5.

Scheme 5

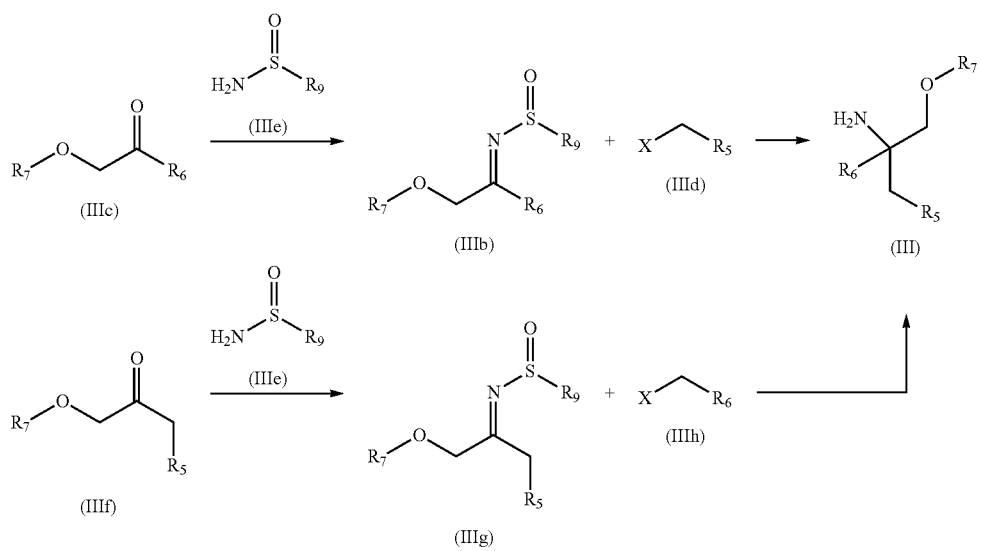

Alternatively, amines of formula (III) can be also prepared by the sequences shown in scheme 6:
1) Reduction of amino acids of formula (VIb) with a reducing agent such as LiAlH4 in an inert solvent like THF to form amino alcohols of formula (VIa), followed by sulfonylation, ring closure to an aziridine of formula (VI), ring opening of the aziridine with an alcohol and removal of the sulfonyl group as described in *Eur. J. Org. Chem.* 2011, 3126-3130.
2) Aziridination of olefins of formula (VIc) to form aziridines of formula (VI) with sulfonamides, an oxidizing agent and a rhodium catalyst as described in *Org. Lett.*, 2005, 2787-2790, followed by ring opening of the aziridine with an alcohol and removal of the sulfonyl group as described in the section above.

A large selection of amino acids of formula (VIb) and olefins of formula (VIc) are commercially available and general protocols for their preparation has been reported in the chemical literature and are known to a person skilled in the art.

Alternatively, certain amines of formula (IIIk) can be prepared from olefins of formula (VII) by treatment with sodium trifluoromethyl sulfinate, an aryl diazonium salt such as benzenediazonium fluoroborate and a catalyst such as silver nitrate, followed by reduction of the resulting azo compounds of formula (VIIa) with raney nickel under a hydrogen atmosphere in a solvent such as ethanol at temperatures between 0° C. and 100° C. This is shown in scheme 7 and described in *Chem. Commun.* 2016, 52, 8275.

Scheme 6

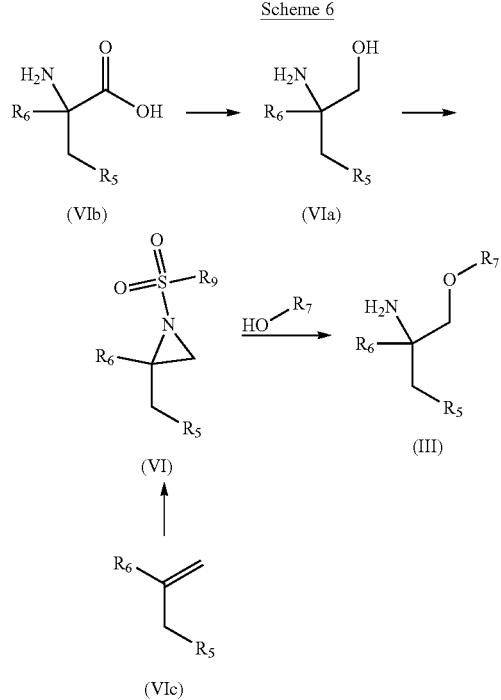

Scheme 7

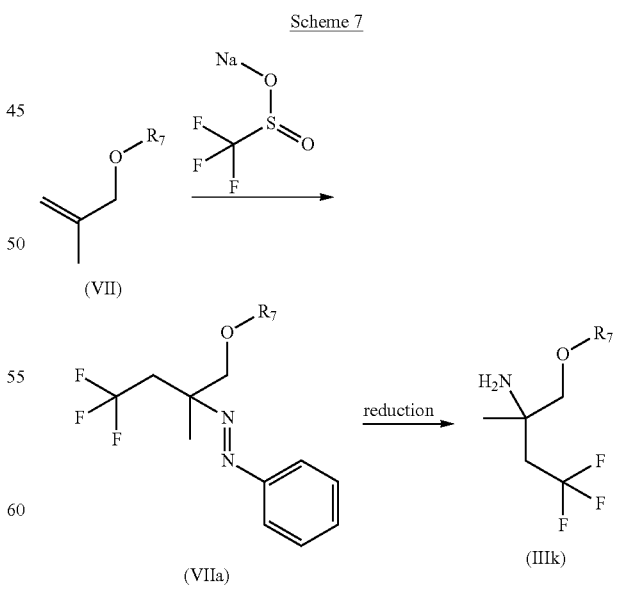

Alternatively, compounds of formula (I-a) can be prepared from compounds of formula (VIII) by treatment with a base such as sodium hydride and an alkylating agent (VIIIa), wherein Y is a leaving groups such as bromide, iodide or methanesulfonate, in an inert solvent such as dimethylformamide. Compounds of formula (VIII) are readily available from the reaction of compounds of formula (VIa) and (II) in the presence of an amide coupling reagent such as propane phosphonic acid anhydride and a base such as triethylamine. This is shown in scheme 8.

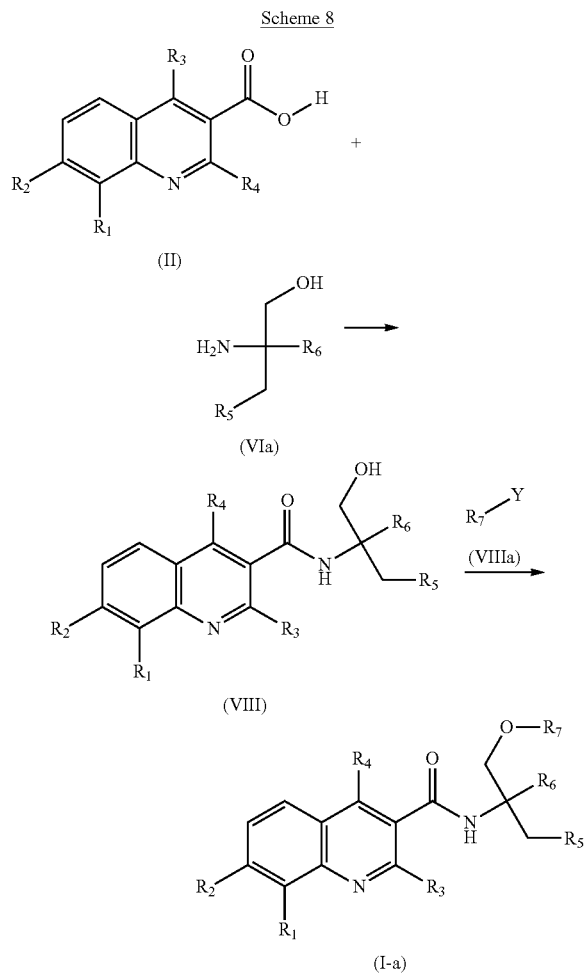

As shown in scheme 9, compounds of general formula (I-b) wherein X is S can be prepared from compounds of general formula (I-a) wherein X is O by treatment with a deoxothionating agent like $P_4S_{10}$ or Lawesson reagent in an inert organic solvent like toluene at temperatures between 20° C. and 150° C.

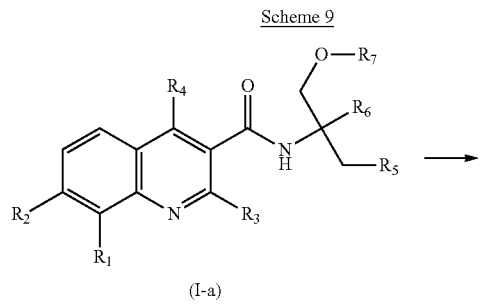

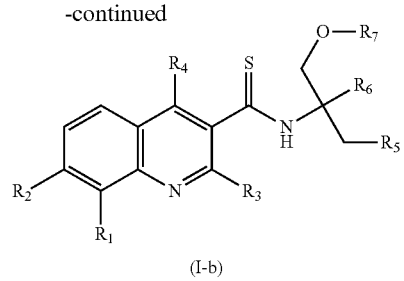

Alternatively, the compounds of formula (I-a) wherein $R_1$, $R_2$, $R_3$, $R_4$, $R_5$, $R_6$ and $R_7$ are as defined for compounds of formula (I) and X is O, can be obtained by transformation of another, closely related, compound of formula (I-a) using standard synthesis techniques known to the person skilled in the art. Non-exhaustive examples include oxidation reactions, reduction reactions, hydrolysis reactions, coupling reactions, aromatic nucleophilic or electrophilic substitution reactions, nucleophilic substitution reactions, nucleophilic addition reactions, cycloaddition reactions and halogenation reactions.

Certain intermediates described in the above schemes are novel and as such form a further aspect of the invention.

The compounds of formula (I) can be used in the agricultural sector and related fields of use e.g. as active ingredients for controlling plant pests or on non-living materials for control of spoilage microorganisms or organisms potentially harmful to man. The novel compounds are distinguished by excellent activity at low rates of application, by being well tolerated by plants and by being environmentally safe. They have very useful curative, preventive and systemic properties and may be used for protecting numerous cultivated plants. The compounds of formula (I) can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula (I) as fungicide. The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It is also possible to use compounds of formula (I) as dressing agents for the treatment of plant propagation material, e.g., seed, such as fruits, tubers or grains, or plant cuttings (for example rice), for the protection against fungal infections as well as against phytopathogenic fungi occurring in the soil. The propagation material can be treated with a composition comprising a compound of formula (I) before planting: seed, for example, can be dressed before being sown. The compounds of formula (I) can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

Furthermore the compounds according to present invention can be used for controlling fungi in related areas, for example in the protection of technical materials, including wood and wood related technical products, in food storage, in hygiene management.

In addition, the invention could be used to protect non-living materials from fungal attack, e.g. lumber, wall boards and paint.

Compounds of formula (I) and fungicidal compositions containing them may be used to control plant diseases caused by a broad spectrum of fungal plant pathogens. They are effective in controlling a broad spectrum of plant diseases, such as foliar pathogens of ornamental, turf, vegetable, field, cereal, and fruit crops.

These fungi and fungal vectors of disease, as well as phytopathogenic bacteria and viruses, which may be controlled are for example:

*Absidia corymbifera*, *Alternaria* spp, *Aphanomyces* spp, *Ascochyta* spp, *Aspergillus* spp. including *A. flavus*, *A. fumigatus*, *A. nidulans*, *A. niger*, *A. terrus*, *Aureobasidium* spp. including *A. pullulans*, *Blastomyces dermatitidis*, *Blumeria graminis*, *Bremia lactucae*, *Botryosphaeria* spp. including *B. dothidea*, *B. obtusa*, *Botrytis* spp. inclusing *B. cinerea*, *Candida* spp. including *C. albicans*, *C. glabrata*, *C. krusei*, *C. lusitaniae*, *C. parapsilosis*, *C. tropicalis*, *Cephaloascus fragrans*, *Ceratocystis* spp, *Cercospora* spp. including *C. arachidicola*, *Cercosporidium personatum*, *Cladosporium* spp, *Claviceps purpurea*,

*Coccidioides immitis*, *Cochliobolus* spp, *Colletotrichum* spp. including *C. musae*,

*Cryptococcus neoformans*, *Diaporthe* spp, *Didymella* spp, *Drechslera* spp, *Elsinoe* spp,

*Epidermophyton* spp, *Erwinia amylovora*, *Erysiphe* spp. including *E. cichoracearum*,

*Eutypa lata*, *Fusarium* spp. including *F. culmorum*, *F. graminearum*, *F. langsethiae*, *F. moniliforme*, *F. oxysporum*, *F. proliferatum*, *F. subglutinans*, *F. solani*, *Gaeumannomyces graminis*, *Gibberella fujikuroi*, *Gloeodes pomigena*, *Gloeosporium musarum*, *Glomerella cingulate*, *Guignardia bidwellii*, *Gymnosporangium juniperi-virginianae*, *Helminthosporium* spp, *Hemileia* spp, *Histoplasma* spp. including *H. capsulatum*, *Laetisaria fuciformis*, *Leptographium lindbergi*, *Leveillula taurica*, *Lophodermium seditiosum*, *Microdochium nivale*, *Microsporum* spp, *Monilinia* spp, *Mucor* spp, *Mycosphaerella* spp. including *M. graminicola*, *M. pomi*, *Oncobasidium theobromaeon*, *Ophiostoma piceae*, *Paracoccidioides* spp, *Penicillium* spp. including *P. digitatum*, *P. italicum*, *Petriellidium* spp, *Peronosclerospora* spp. Including *P. maydis*, *P. philippinensis* and *P. sorghi*, *Peronospora* spp, *Phaeosphaeria nodorum*, *Phakopsora pachyrhizi*, *Phellinus igniarus*, *Phialophora* spp, *Phoma* spp, *Phomopsis viticola*, *Phytophthora* spp. including *P. infestans*, *Plasmopara* spp. including *P. halstedii*, *P. viticola*, *Pleospora* spp., *Podosphaera* spp. including *P. leucotricha*, *Polymyxa graminis*, *Polymyxa betae*, *Pseudocercosporella herpotrichoides*, *Pseudomonas* spp, *Pseudoperonospora* spp. including *P. cubensis*, *P. humuli*, *Pseudopeziza tracheiphila*, *Puccinia* Spp. including *P. hordei*, *P. recondita*, *P. striiformis*, *P. triticina*, *Pyrenopeziza* spp, *Pyrenophora* spp, *Pyricularia* spp. including *P. oryzae*, *Pythium* spp. including *P. ultimum*, *Ramularia* spp, *Rhizoctonia* spp, *Rhizomucor pusillus*, *Rhizopus arrhizus*, *Rhynchosporium* spp, *Scedosporium* spp. including *S. apiospermum* and *S. prolificans*, *Schizothyrium pomi*,

*Sclerotinia* spp, *Sclerotium* spp, *Septoria* spp, including *S. nodorum*, *S. tritici*, *Sphaerotheca macularis*, *Sphaerotheca fusca* (*Sphaerotheca fuliginea*), *Sporothorix* spp, *Stagonospora nodorum*, *Stemphylium* spp., *Stereum hirsutum*, *Thanatephorus cucumeris*, *Thielaviopsis basicola*, *Tilletia* spp, *Trichoderma* spp. including *T. harzianum*, *T. pseudokoningii*, *T. viride*,

*Trichophyton* spp, *Typhula* spp, *Uncinula necator*, *Urocystis* spp, *Ustilago* spp, *Venturia* spp. including *V. inaequalis*, *Verticillium* spp, and *Xanthomonas* spp.

In particular, compounds of formula (I) and fungicidal compositions containing them may be used to control plant diseases caused by a broad spectrum of fungal plant pathogens in the Basidiomycete, Ascomycete, Oomycete and/or Deuteromycete, Blasocladiomycete, Chrytidiomycete, Glomeromycete and/or Mucoromycete classes.

These pathogens may include: Oomycetes, including *Phytophthora* diseases such as those caused by *Phytophthora capsici*, *Phytophthora infestans*, *Phytophthora sojae*, *Phytophthora fragariae*, *Phytophthora nicotianae*, *Phytophthora cinnamomi*, *Phytophthora citricola*, *Phytophthora citrophthora* and *Phytophthora erythroseptica*; *Pythium* diseases such as those caused by *Pythium aphanidermatum*, *Pythium arrhenomanes*, *Pythium graminicola*, *Pythium irregulare* and *Pythium ultimum*; diseases caused by Peronosporales such as *Peronospora destructor*, *Peronospora parasitica*, *Plasmopara viticola*, *Plasmopara halstedii*, *Pseudoperonospora cubensis*, *Albugo candida*, *Sclerophthora macrospora* and *Bremia lactucae*; and others such as *Aphanomyces cochlioides*, *Labyrinthula zosterae*, *Peronosclerospora sorghi* and *Sclerospora graminicola*.

Ascomycetes, including blotch, spot, blast or blight diseases and/or rots for example those caused by Pleosporales such as *Stemphylium solani*, *Stagonospora tainanensis*, *Spilocaea oleaginea*, *Setosphaeria turcica*, *Pyrenochaeta lycoperisici*, *Pleospora herbarum*, *Phoma destructiva*, *Phaeosphaeria herpotrichoides*, *Phaeocryptocus gaeumannii*, *Ophiosphaerella graminicola*, *Ophiobolus graminis*, *Leptosphaeria maculans*, *Hendersonia creberrima*, *Helminthosporium triticirepentis*, *Setosphaeria turcica*, *Drechslera glycines*, *Didymella bryoniae*, *Cycloconium oleagineum*, *Corynespora cassiicola*, *Cochliobolus sativus*, *Bipolaris cactivora*, *Venturia inaequalis*, *Pyrenophora teres*, *Pyrenophora tritici-repentis*, *Alternaria alternata*, *Alternaria brassicicola*, *Alternaria solani* and *Alternaria tomatophila*, Capnodiales such as *Septoria tritici*, *Septoria nodorum*, *Septoria glycines*, *Cercospora arachidicola*, *Cercospora sojina*, *Cercospora zeae-maydis*, *Cercosporella capsellae* and *Cercosporella herpotrichoides*, *Cladosporium carpophilum*, *Cladosporium effusum*, *Passalora fulva*, *Cladosporium oxysporum*, *Dothistroma septosporum*, *Isariopsis clavispora*, *Mycosphaerella fijiensis*, *Mycosphaerella graminicola*, *Mycovellosiella koepkeii*, *Phaeoisariopsis bataticola*, *Pseudocercospora vitis*, *Pseudocercosporella herpotrichoides*, *Ramularia beticola*, *Ramularia collo-cygni*, Magnaporthales such as *Gaeumannomyces graminis*, *Magnaporthe grisea*, *Pyricularia oryzae*, Diaporthales such as *Anisogramma anomala*, *Apiognomonia errabunda*, *Cytospora platani*, *Diaporthe phaseolorum*, *Discula destructiva*, *Gnomonia fructicola*, *Greeneria uvicola*, *Melanconium juglandinum*, *Phomopsis viticola*, *Sirococcus clavigignenti-juglandacearum*, *Tubakia dryina*, *Dicarpella* spp., *Valsa ceratosperma*, and others such as *Actinothyrium graminis*, *Ascochyta pisi*, *Aspergillus flavus*, *Aspergillus fumigatus*, *Aspergillus nidulans*, *Asperisporium caricae*, *Blumeriella jaapii*, *Candida* spp., *Capnodium ramosum*, *Cephaloascus* spp., *Cephalosporium gramineum*, *Ceratocystis paradoxa*, *Chaetomium* spp., *Hymenoscyphus pseudoalbidus*, *Coccidioides* spp., *Cylindrosporium padi*, *Diplocarpon malae*, *Drepanopeziza campestris*, *Elsinoe*

*ampelina, Epicoccum nigrum, Epidermophyton* spp., *Eutypa lata, Geotrichum candidum, Gibellina cerealis, Gloeocercospora sorghi, Gloeodes pomigena, Gloeosporium perennans; Gloeotinia temulenta, Griphospaeria corticola, Kabatiella lini, Leptographium microsporum, Leptosphaerulinia crassiasca, Lophodermium seditiosum, Marssonina graminicola, Microdochium nivale, Monilinia fructicola, Monographella albescens, Monosporascus cannonballus, Naemacyclus* spp., *Ophiostoma novo-ulmi, Paracoccidioides brasiliensis, Penicillium expansum, Pestalotia rhododendri, Petriellidium* spp., *Pezicula* spp., *Phialophora gregata, Phyllachora pomigena, Phymatotrichum omnivora, Physalospora abdita, Plectosporium tabacinum, Polyscytalum pustulans, Pseudopeziza medicaginis, Pyrenopeziza brassicae, Ramulispora sorghi, Rhabdocline pseudotsugae, Rhynchosporium secalis, Sacrocladium oryzae, Scedosporium* spp., *Schizothyrium pomi, Sclerotinia sclerotiorum, Sclerotinia minor Sclerotium* spp., *Typhula ishikariensis, Seimatosporium mariae, Lepteutypa cupressi, Septocyta ruborum, Sphaceloma perseae, Sporonema phacidioides, Stigmina palmivora, Tapesia yallundae, Taphrina bullata, Thielviopsis basicola, Trichoseptoria fructigena, Zygophiala jamaicensis*; powdery mildew diseases for example those caused by Erysiphales such as *Blumeria graminis, Erysiphe polygoni, Uncinula necator, Sphaerotheca fuligena, Podosphaera leucotricha, Podospaera macularis Golovinomyces cichoracearum, Leveillula taurica, Microsphaera diffusa, Oidiopsis gossypii, Phyllactinia guttata* and *Oidium arachidis*; molds for example those caused by Botryosphaeriales such as *Dothiorella aromatica, Diplodia seriata, Guignardia bidwellii, Botrytis cinerea, Botryotinia allii, Botryotinia fabae, Fusicoccum amygdali, Lasiodiplodia theobromae, Macrophoma theicola, Macrophomina phaseolina, Phyllosticta cucurbitacearum*; anthracnoses for example those caused by Glommerelales such as *Colletotrichum gloeosporioides, Colletotrichum lagenarium, Colletotrichum gossypii, Glomerella cingulata,* and *Colletotrichum graminicola*; and wilts or blights for example those caused by Hypocreales such as *Acremonium strictum, Claviceps purpurea, Fusarium culmorum, Fusarium graminearum, Fusarium virguliforme, Fusarium oxysporum, Fusarium subglutinans, Fusarium oxysporum* f. sp. *cubense, Gerlachia nivale, Gibberella fujikuroi, Gibberella zeae, Gliocladium* spp., *Myrothecium verrucaria, Nectria ramulariae, Trichoderma viride, Trichothecium roseum,* and *Verticillium theobromae.*

Basidiomycetes, including smuts for example those caused by Ustilaginales such as *Ustilaginoidea virens, Ustilago nuda, Ustilago tritici, Ustilago zeae,* rusts for example those caused by Pucciniales such as *Cerotelium fici, Chrysomyxa arctostaphyli, Coleosporium ipomoeae, Hemileia vastatrix, Puccinia arachidis, Puccinia cacabata, Puccinia graminis, Puccinia recondita, Puccinia sorghi, Puccinia hordei, Puccinia striiformis* f. sp. *Hordei, Puccinia striiformis* f. sp. *Secalis, Pucciniastrum coryli,* or Uredinales such as *Cronartium ribicola, Gymnosporangium juniperi-viginianae, Melampsora medusae, Phakopsora pachyrhizi, Phragmidium mucronatum, Physopella ampelosidis, Tranzschelia discolor* and *Uromyces viciae-fabae*; and other rots and diseases such as those caused by *Cryptococcus* spp., *Exobasidium vexans, Marasmiellus inoderma, Mycena* spp., *Sphacelotheca reiliana, Typhula ishikariensis, Urocystis agropyri, Itersonilia perplexans, Corticium invisum, Laetisaria fuciformis, Waitea circinata, Rhizoctonia solani, Thanetephorus cucurmeris, Entyloma dahliae, Entylomella microspora, Neovossia moliniae* and *Tilletia caries.*

Blastocladiomycetes, such as *Physoderma maydis.*

Mucoromycetes, such as *Choanephora cucurbitarum; Mucor* spp.; *Rhizopus arrhizus,*

As well as diseases caused by other species and genera closely related to those listed above.

In addition to their fungicidal activity, the compounds and compositions comprising them may also have activity against bacteria such as *Erwinia amylovora, Erwinia caratovora, Xanthomonas campestris, Pseudomonas syringae, Streptomyces* scabies and other related species as well as certain protozoa.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and *Zoysia* grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The useful plants and/or target crops in accordance with the invention include conventional as well as genetically enhanced or engineered varieties such as, for example, insect resistant (e.g. Bt. and VIP varieties) as well as disease resistant, herbicide tolerant (e.g. glyphosate- and glufosinate-resistant maize varieties commercially available under the trade names RoundupReady® and LibertyLink®) and nematode tolerant varieties. By way of example, suitable genetically enhanced or engineered crop varieties include the Stoneville 5599BR cotton and Stoneville 4892BR cotton varieties.

The term "useful plants" and/or "target crops" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" and/or "target crops" is to be understood as including those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi. An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

The term "useful plants" and/or "target crops" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Toxins that can be expressed by transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

Further, in the context of the present invention there are to be understood by 6-endotoxins, for example Cry1Ab, Cry1Ac, Cry1F, Cry1 Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO03/018810).

More examples of such toxins or transgenic plants capable of synthesising such toxins are disclosed, for example, in EP-A-0 374 753, WO93/07278, WO95/34656, EP-A-0 427 529, EP-A-451 878 and WO03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1 Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

Pesticidal agents referred to herein using their common name are known, for example, from "The Pesticide Manual", 15th Ed., British Crop Protection Council 2009.

The compounds of formula (I) may be used in unmodified form or, preferably, together with the adjuvants conventionally employed in the art of formulation. To this end they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g. for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

Suspension concentrates are aqueous formulations in which finely divided solid particles of the active compound are suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from 0.5% to 95% of the concentrate.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain from 5% to 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from 0.5% to 95% of the concentrate.

Granular formulations include both extrudates and relatively coarse particles and are usually applied without dilution to the area in which treatment is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain 5% to 25% of active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically 1 to 50 microns in diameter. The enclosed liquid typically constitutes 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre and preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Suitable agricultural adjuvants and carriers that are useful in formulating the compositions of the invention in the formulation types described above are well known to those skilled in the art.

Liquid carriers that can be employed include, for example, water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc., ethylene glycol, propylene glycol, glycerine and N-methyl-2-pyrrolidinone. Water is generally the carrier of choice for the dilution of concentrates.

Suitable solid carriers include, for example, talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour and lignin.

A broad range of surface-active agents are advantageously employed in both said liquid and solid compositions, especially those designed to be diluted with carrier before application. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, anti-foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants and sticking agents.

In addition, further, other biocidally active ingredients or compositions may be combined with the compositions of the invention and used in the methods of the invention and applied simultaneously or sequentially with the compositions of the invention. When applied simultaneously, these further active ingredients may be formulated together with the compositions of the invention or mixed in, for example, the spray tank. These further biocidally active ingredients may be fungicides, herbicides, insecticides, bactericides, acaricides, nematicides and/or plant growth regulators.

In addition, the compositions of the invention may also be applied with one or more systemically acquired resistance inducers ("SAR" inducer). SAR inducers are known and described in, for example, U.S. Pat. No. 6,919,298 and include, for example, salicylates and the commercial SAR inducer acibenzolar-S-methyl.

The compounds of formula (I) are normally used in the form of compositions and can be applied to the crop area or plant to be treated, simultaneously or in succession with further compounds. These further compounds can be e.g. fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be used in the form of (fungicidal) compositions for controlling or protecting against phytopathogenic microorganisms, comprising as active ingredient at least one compound of formula (I) or of at least one preferred individual compound as above-defined, in free form or in agrochemically usable salt form, and at least one of the above-mentioned adjuvants.

The invention therefore provides a composition, preferably a fungicidal composition, comprising at least one compound formula (I) an agriculturally acceptable carrier and optionally an adjuvant. An agricultural acceptable carrier is for example a carrier that is suitable for agricultural use. Agricultural carriers are well known in the art. Preferably said composition may comprise at least one or more pesticidally active compounds, for example an additional fungicidal active ingredient in addition to the compound of formula (I).

The compound of formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities.

Examples of suitable additional active ingredients include the following: 1,2,4-thiadiazoles, 2,6-dinitroanilines, acyl-alanines, aliphatic nitrogenous compounds, amidines, aminopyrimidinols, anilides, anilino-pyrimidines, anthraquinones, antibiotics, aryl-phenylketones, benzamides, benzenesulfonamides, benzimidazoles, benzothiazoles, benzothiodiazoles, benzothiophenes, benzoylpyridines, benzthiadiazoles, benzylcarbamates, butylamines, carbamates, carboxamides, carpropamids, chloronitriles, cinnamic acid amides, copper containing compounds, cyanoacetamideoximes, cyanoacrylates, cyanoimidazoles, cyanomethylenethiazolidines, dicarbonitriles, dicarboxamides, dicarboximides, dimethylsulphamates, dinitrophenol carbonates, dinitrophenysl, dinitrophenyl crotonates, diphenyl phosphates, dithiino compounds, dithiocarbamates, dithioethers, dithiolanes, ethyl-amino-thiazole carboxamides, ethyl-phosphonates, furan carboxamides, glucopyranosyls, glucopyranoxyls, glutaronitriles, guanidines, herbicides/plant growth regulatosr, hexopyranosyl antibiotics, hydroxy(2-amino)pyrimidines, hydroxyanilides, hydroxyisoxazoles, imidazoles, imidazolinones, insecticides/plant growth regulators, isobenzofuranones, isoxazolidinyl-pyridines, isoxazolines, maleimides, mandelic acid amides, mectin derivatives, morpholines, norpholines, n-phenyl carbamates, organotin compounds, oxathiin carboxamides, oxazoles, oxazolidine-diones, phenols, phenoxy quinolines, phenyl-acetamides, phenylamides, phenylbenzamides, phenyl-oxo-ethyl-thiophenes amides, phenylpyrroles, phenylureas, phosphorothiolates, phosphorus acids, phthalamic acids, phthalimides, picolinamides, piperazines, piperidines, plant extracts, polyoxins, propionamides, pthalimides, pyrazole-4-carboxamides, pyrazolinones, pyridazinones, pyridines, pyridine carboxamides, pyridinyl-ethyl benzamides, pyrimdinamines, pyrimidines, pyrimidine-amines, pyrimidione-hydrazone, pyrrolidines, pyrrolquinoliones, quinazolinones, quinolines, quinoline derivatives, quinoline-7-carboxylic acids, quinoxalines, spiroketalamines, strobilurins, sulfamoyl triazoles, sulphamides, tetrazolyloximes, thiadiazines, thiadiazole carboxamides, thiazole carboxanides, thiocyanates, thiophene carboxamides, toluamides, triazines, triazobenthiazoles, triazoles, triazole-thiones, triazolo-pyrimidylamine, valinamide carbamates, ammonium methyl phosphonates, arsenic-containing compounds, benyimidazolylcarbamates, carbonitriles, carboxanilides, carboximidamides, carboxylic phenylamides, diphenyl pyridines, furanilides, hydrazine carboxamides, imidazoline acetates, isophthalates, isoxazolones, mercury salts, organomercury compounds, organophosphates, oxazolidinediones, pentylsulfonyl benzenes, phenyl benzamides, phosphonothionates, phosphorothioates, pyridyl carboxamides, pyridyl furfuryl ethers, pyridyl methyl ethers, SDHIs, thiadiazinanethiones, thiazolidines.

A further aspect of invention is related to a method of controlling or preventing an infestation of plants, e.g. useful plants such as crop plants, propagation material thereof, e.g. seeds, harvested crops, e.g. harvested food crops, or of non-living materials by phytopathogenic or spoilage microorganisms or organisms potentially harmful to man, especially fungal organisms, which comprises the application of a compound of formula (I) or of a preferred individual compound as above-defined as active ingredient to the plants, to parts of the plants or to the locus thereof, to the propagation material thereof, or to any part of the non-living materials.

Controlling or preventing means reducing infestation by insects or by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of formula (I), or an agrochemical composition which contains at least one of said compounds, is foliar application. The frequency of application and the rate of application will depend on the risk of infestation by the corresponding pathogen or insect. However, the compounds of formula (I) can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation, e.g. a composition containing the compound of formula (I), and, if desired, a solid or liquid adjuvant or monomers for encapsulating the compound of formula (I), may be prepared in a known manner, typically by intimately mixing and/or grinding the compound with extenders, for example solvents, solid carriers and, optionally, surface active compounds (surfactants).

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is preferably 1 g to 2000 g of active ingredient per hectare, more preferably 10 to 1000 g/ha, most preferably 10 to 600 g/ha. When used as seed drenching agent, convenient dosages are from 10 mg to 1 g of active substance per kg of seeds.

When the combinations of the present invention are used for treating seed, rates of 0.001 to 50 g of a compound of formula (I) per kg of seed, preferably from 0.01 to 10 g per kg of seed are generally sufficient.

Suitably, a composition comprising a compound of formula (I) according to the present invention is applied either preventative, meaning prior to disease development or curative, meaning after disease development.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the ondensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) together with component (B) and (C), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Whereas it is preferred to formulate commercial products as concentrates, the end user will normally use dilute formulations.

EXAMPLES

The Examples which follow serve to illustrate the invention. Certain compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm or 0.2 ppm.

Throughout this description, temperatures are given in degrees Celsius and "m.p." means melting point. LC/MS means Liquid Chromatography Mass Spectroscopy and the description of the apparatus and the methods are:

Method G:

Spectra were recorded on a Mass Spectrometer from Waters (SQD, SQDII Single quadrupole mass spectrometer) equipped with an electrospray source (Polarity: positive and negative ions), Capillary: 3.00 kV, Cone range: 30 V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) and an Acquity UPLC from Waters: Binary pump, heated column compartment, diode-array detector and ELSD detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 1.2 min; Flow (ml/min) 0.85

Method H:

Spectra were recorded on a Mass Spectrometer from Waters (SQD, SQDII Single quadrupole mass spectrometer) equipped with an electrospray source (Polarity: positive and negative ions), Capillary: 3.00 kV, Cone range: 30V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) and an Acquity UPLC from Waters: Binary pump, heated column compartment, diode-array detector and ELSD detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 2.7 min; Flow (ml/min) 0.85

Method W:

Spectra were recorded on a Mass Spectrometer (ACQUITY UPLC) from Waters (SQD, SQDII Single quadrupole mass spectrometer) equipped with an electrospray source (Polarity: positive or negative ions, Capillary: 3.0 kV, Cone: 30V, Extractor: 3.00 V, Source Temperature: 150° C., Desolvation Temperature: 400° C., Cone Gas Flow: 60 L/Hr, Desolvation Gas Flow: 700 L/Hr, Mass range: 140 to 800 Da), DAD Wavelength range (nm): 210 to 400, and an Acquity UPLC from Waters: Solvent degasser, binary pump, heated column compartment and diode-array detector. Column: Waters UPLC HSS T3, 1.8 m, 30×2.1 mm, Temp: 60° C., DAD Wavelength range (nm): 210 to 500, Solvent Gradient: A=Water/Methanol 9:1, 0.1% formic acid, B=Acetonitrile+0.1% formic acid, gradient: 0-100% B in 2.5 min; Flow (ml/min) 0.75

Formulation Examples

| Wettable powders | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The active ingredient is thoroughly mixed with the adjuvants and the mixture is thoroughly ground in a suitable mill, affording powders that can be used directly for seed treatment.

Emulsifiable Concentrate

| | |
|---|---|
| active ingredient [compound of formula(I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [compound of formula (I)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

Extruder Granules

| | |
|---|---|
| Active ingredient [compound of formula (I)] | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

Coated Granules

| | |
|---|---|
| Active ingredient [compound of formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

Suspension Concentrate

| | |
|---|---|
| active ingredient [compound of formula (I)] | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredient [compound of formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula (I) are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

Preparation Examples

Example 1: Preparation of N-[1-(cyclohexoxymethyl)-3,3,3-trifluoro-1-methyl-propyl]-8-fluoro-quinoline-3-carboxamide Step 1, preparation of 2-methylallyloxycyclohexane To a suspension of sodium hydride (60%, 1.75 g, 43.9 mmol) in tetrahydrofuran (40 mL)/dimethyl formamide (4 mL) was added cyclohexanol (4.0 g, 39.9 mmol) at 5-10° C. The resulting mixture was warmed to room temperature and stirred for 30 minutes. 3-bromo-2-methyl-prop-1-ene (5.7 g, 41.9 mmol) was added slowly and the reaction aged for 24 h at 20° C. Water was then added carefully and the mixture was extracted with methyl tertbutyl ether. The organic layer was washed with water, brine, dried over MgSO4, filtrated and concentrated in vacuo. The residual oil was filtrated through a short silica plug (rinsed with cyclohexane/ethyl acetate) to give the title compound as colorless liquid.

$^{1}$H NMR (400 MHz, CDCl$_{3}$) δ 4.97-4.99 (m, 1H), 4.85-4.87 (m, 1H), 3.91 (s, 2H), 3.22-3.30 (m, 1H), 1.84-1.98 (m, 2H), 1.67-1.82 (m, 5H), 1.13-1.39 (m, 6H).

Step 2, preparation of [1-(cyclohexoxymethyl)-3,3,3-trifluoro-1-methyl-propyl]-phenyl-diazene

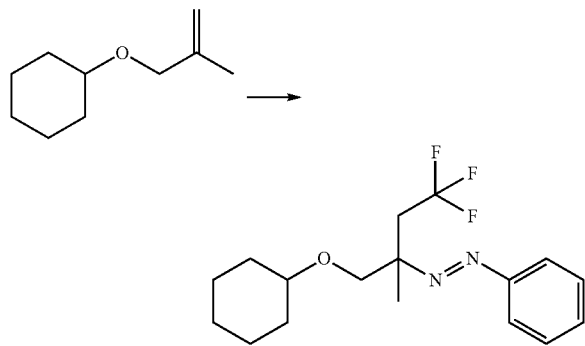

2-methylallyloxycyclohexane (0.8 g, 5.0 mmol) was added to a solution of sodium trifluoromethylsulfinate (2.0 g 10 mmol) in acetonitrile (20 mL). To this was added sequentially benzenediazonium fluoroborate (1 M in acetonitrile, 10 mL, 10 mmol), CuBF$_{4}$-(MeCN)$_{4}$ (0.08 g, 0.3 mmol) and H$_{2}$O$_{2}$ (aq. 30%, 0.06 g) at RT. The resulting mixture was stirred for 18 h at room temperature after which time no further gas evolution was observed. The brown-red suspension was diluted with water and extracted with cyclohexane. The organic layer was washed with water, brine, dried over MgSO4, filtrated and concentrated in vacuo. The residue was purified by medium pressure chromatography through silica gel (cyclohexane/ethyl acetate) to afford the title compound as yellow, viscous oil.

$^{1}$H NMR (400 MHz, CDCl$_{3}$) δ 7.59-7.73 (m, 2H), 7.33-7.54 (m, 3H), 3.80 (d, 1H), 3.60 (d, 1H), 3.20-3.25 (m, 1H), 2.74-2.99 (m, 2H), 1.62-1.89 (m, 4H), 1.45 (s, 3H), 1.13-1.38 (m, 6H).

$^{19}$F NMR (376 MHz, CDCl$_{3}$) δ -59.4.

Step 3, preparation of 1-(cyclohexoxy)-4,4,4-trifluoro-2-methyl-butan-2-amine

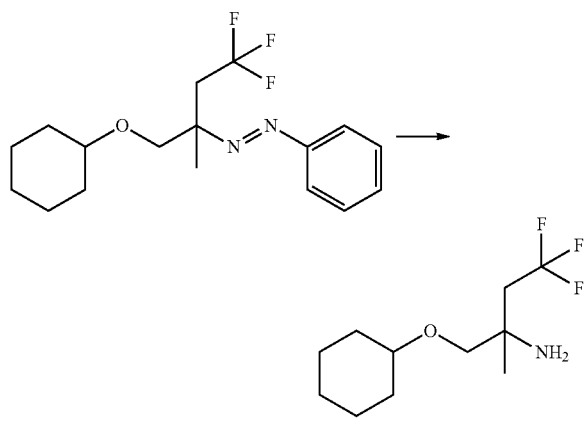

To a solution of [1-(cyclohexoxymethyl)-3,3,3-trifluoro-1-methyl-propyl]-phenyl-diazene (0.32 g, 0.97 mmol) in ethanol (15 mL) was added Raney nickel (aq. slurry, ca. 0.8 g) and the resulting mixture was stirred for 1 h at 65° C. under hydrogen atmosphere (1 bar). The resulting colorless emulsion was cooled to 20° C., filtrated through Celite and the filtrate was concentrated in vacuo. The residue was taken up in aq. HCl (1 M) and washed with cyclohexane. The aqueous layer was basified to pH 12 with aq. NaOH and extracted with methyl tertbutylether. The organic layer was washed with brine, dried over MgSO4, filtrated and concentrated in vacuo to afford a mixture of the title compound and aniline which was used as such for the next step. An analytically pure sample was obtained by medium pressure chromatography (silica gel, cyclohexane/EtOAc).

$^{1}$H NMR (400 MHz, CDCl$_{3}$) δ 3.23-3.34 (m, 2H), 3.21 (d, 1H), 2.31 (dq, 2H), 1.65-1.92 (m, 4H), 1.22-1.61 (m, 6H), 1.20 (s, 3H)

$^{19}$F NMR (376 MHz, CDCl$_{3}$) δ -59.9

Step 4, preparation of N-[1-(cyclohexoxymethyl)-3,3,3-trifluoro-1-methyl-propyl]-8-fluoro-quinoline-3-carboxamide

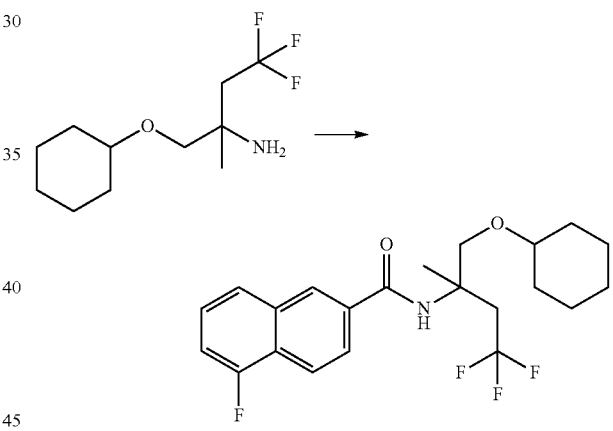

A suspension of 8-fluoroquinoline-3-carboxylic acid (0.17 g, 0.87 mmol) in acetonitrile (1.5 mL) was treated with triethylamine (0.28 mL, 2 mmol) and propylphosphonic anhydride (50% in ethyl acetate, 0.8 mL, 1.3 mmol) at 20° C. The resulting solution was aged for 5 min before a solution of 1-(cyclohexoxy)-4,4,4-trifluoro-2-methyl-butan-2-amine (0.16 g, 0.67 mmol) in acetonitrile (1.5 mL) was added. The reaction was stirred for 1 h at 20° C., diluted with water and extracted with ethyl acetate. The organic layer was washed with aq. NaHCO$_{3}$, NH$_{4}$Cl and brine, dried over MgSO$_{4}$, filtrated and concentrated in vacuo. The residue was purified by medium pressure chromatography (silica gel, cyclohexane/EtOAc) to afford the title compound as white solid.

$^{1}$H NMR (400 MHz, CDCl$_{3}$) δ 9.23 (d, 1H), 8.59 (t, 1H), 7.41-7.82 (m, 3H), 6.74 (s, 1H), 3.74 (d, 1H), 3.61 (d, 1H), 3.34-3.44 (m, 1H), 3.03-3.16 (m, 1H), 2.74-2.95 (m, 1H), 1.69-1.99 (m, 4H), 1.68 (s, 3H), 1.19-1.40 (m, 6H)

$^{19}$F NMR (376 MHz, CDCl$_{3}$) δ -60.2, -124.6

TABLE E

Physical data of compounds of formula (I)

| Entry | IUPAC Name | Structure | RT (min) | [M + H] (measured) | Method | MP ° C. |
|---|---|---|---|---|---|---|
| E.001 | N-[1-(2,2-dimethyl-propoxymethyl)-3,3,3-trifluoro-1-methyl-propyl]-8-fluoro-quinoline-3-carboxamide | 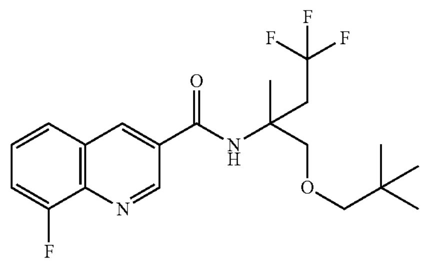 [SMILES: CC(C)(C)COCC(C)(CC(F)(F)F)NC(=O)c1cnc2c(F)cccc2c1] | 1.20 | 401 | G | 74-78 |
| E.002 | 8-chloro-N-[1-[(3,3-dimethyl-cyclobutoxy)-methyl]-3,3,3-trifluoro-1-methylpropyl]-quinoline-3-carboxamide | 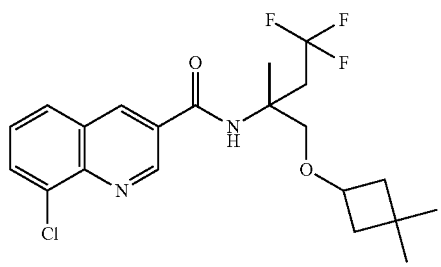 [SMILES: CC1(C)CC(OCC(C)(CC(F)(F)F)NC(=O)c2cnc3c(Cl)cccc3c2)C1] | 1.23 | 429 | G | 127-130 |
| E.003 | N-[1-[(4,4-difluoro-cyclohexoxy)-methyl]-3,3,3-trifluoro-1-methyl-propyl]-8-fluoro-quinoline-3-carboxamide | 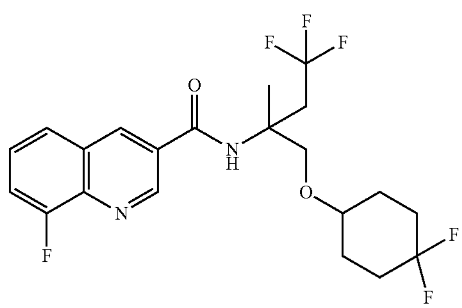 [SMILES: CC(COC1CCC(F)(F)CC1)(CC(F)(F)F)NC(=O)c1cnc2c(F)cccc2c1] | 1.11 | 450 | G | 42-44 |
| E.004 | N-[1-[(3,3-dimethyl-cyclobutoxy)-methyl]-3,3,3-trifluoro-1-methyl-propyl]-8-fluoro-quinoline-3-carboxamide | 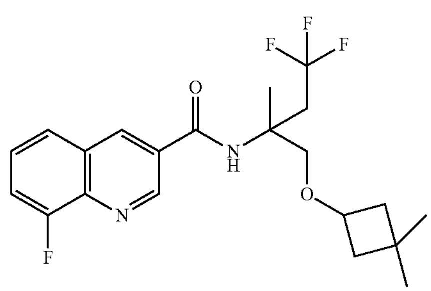 [SMILES: CC1(C)CC(OCC(C)(CC(F)(F)F)NC(=O)c2cnc3c(F)cccc3c2)C1] | 1.19 | 413 | G | 80-84 |
| E.005 | N-[1-[(4-chloro-phenoxy)methyl]-3,3,3-trifluoro-1-methyl-propyl]-8-fluoro-quinoline-3-carboxamide | 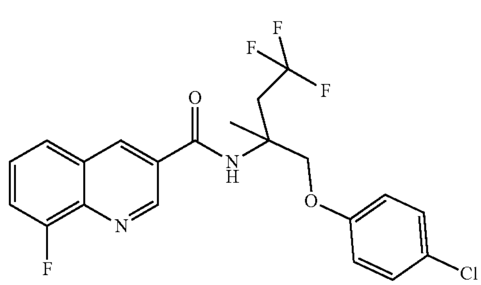 [SMILES: CC(COc1ccc(Cl)cc1)(CC(F)(F)F)NC(=O)c1cnc2c(F)cccc2c1] | 1.14 | 439 | G | 94-96 |

TABLE E-continued

Physical data of compounds of formula (I)

| Entry | IUPAC Name | Structure | RT (min) | [M + H] (measured) | Method | MP °C. |
|---|---|---|---|---|---|---|
| E.006 | N-[1-(cyclo-propylmethoxy-methyl)-1,3,3-trimethylbutyl]-8-fluoro-quinoline-3-carboxamide | 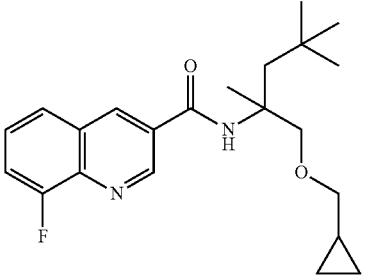 [SMILES: CC(C)(C)CC(C)(COCC1CC1)NC(=O)c1cnc2c(F)cccc2c1] | 1.16 | 373 | G | |
| E.007 | N-[1-(cyclo-butoxymethyl)-3,3,3-trifluoro-1-methyl-propyl]-8-fluoro-4-methyl-quinoline-3-carboxamide | 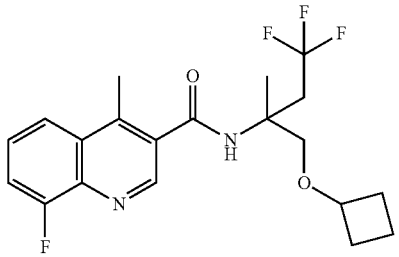 [SMILES: Cc1c(C(=O)NC(C)(COC2CCC2)CC(F)(F)F)cnc2c(F)cccc12] | 1.09 | 399 | G | |
| E.008 | N-[1-(cyclo-butoxymethyl)-3,3,3-trifluoro-1-methyl-propyl]-7,8-difluoro-quinoline-3-carboxamide | 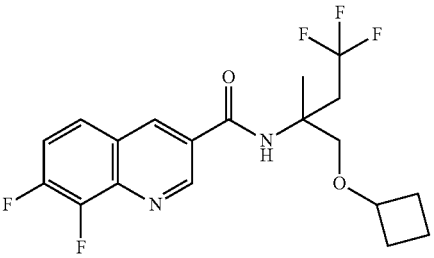 [SMILES: CC(COC1CCC1)(CC(F)(F)F)NC(=O)c1cnc2c(F)c(F)ccc2c1] | 1.11 | 403 | G | |
| E.009 | N-[1-(cyclo-butoxymethyl)-3,3,3-trifluoro-1-methyl-propyl]-8-fluoro-2-methyl-qiuinoline-3-carboxamide | 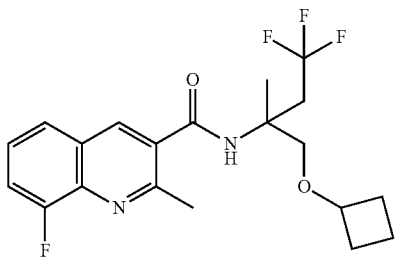 [SMILES: Cc1nc2c(F)cccc2cc1C(=O)NC(C)(COC1CCC1)CC(F)(F)F] | 1.10 | 399 | G | |
| E.010 | 8-fluoro-N-[3,3,3-[trifluoro-1-methyl-1-[(1-methylcyclo-pentoxy)methyl]-propyl]quinoline-3-carboxamide | 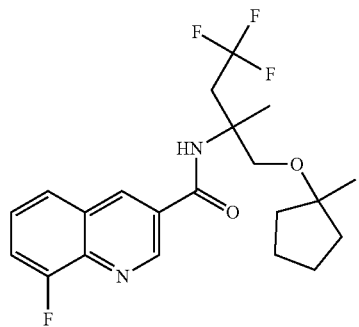 [SMILES: CC(COC1(C)CCCC1)(CC(F)(F)F)NC(=O)c1cnc2c(F)cccc2c1] | 1.19 | 413 | G | |

TABLE E-continued

Physical data of compounds of formula (I)

| Entry | IUPAC Name | Structure | RT (min) | [M + H] (measured) | Method | MP ° C. |
|---|---|---|---|---|---|---|
| E.011 | N-[1-cyclo-butoxymethyl)-3,3,3-trifluoro-1-methyl-propyl]-8-methyl-quinoline-3-carboxamide | 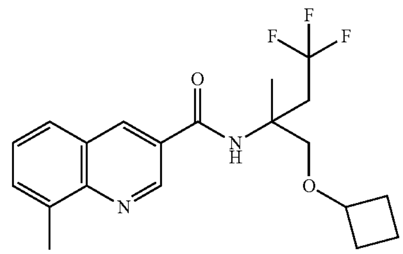 [SMILES: Cc1cccc2cc(C(=O)NC(C)(COC3CCC3)CC(F)(F)F)cnc12] | 1.17 | 381 | G | |
| E.012 | 8-chloro-N-[1-(cyclobutoxymethyl)-3,3,3-trifluoro-1-methyl-propyl]-quinoline-3-carboxamide | 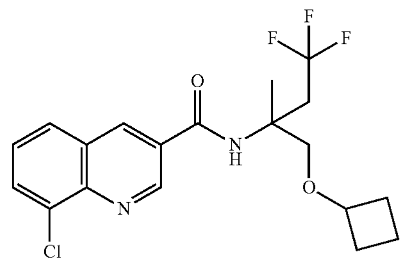 [SMILES: CC(COC1CCC1)(CC(F)(F)F)NC(=O)c1cnc2c(Cl)cccc2c1] | 1.14 | 401 | G | |
| E.013 | N-[(1S)-1-(cyclo-butoxymethyl)-3,3,3-trifluoro-1-methyl-propyl]-8-fluoro-quinoline-3-carboxamide | 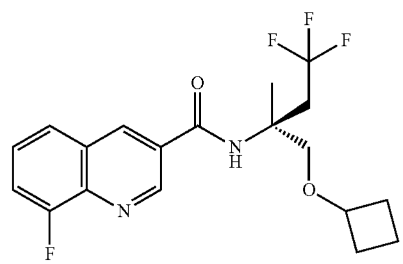 [SMILES: C[C@@](COC1CCC1)(CC(F)(F)F)NC(=O)c1cnc2c(F)cccc2c1] | 1.09 | 385 | G | |
| E.014 | N-[(1S)-1-(cyclo-butoxymethyl)-3,3,3-trifluoro-1-methyl-propyl]-8-fluoro-quinoline-3-carboxamide | 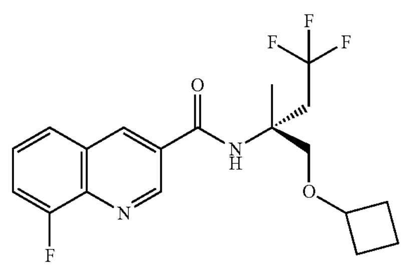 [SMILES: C[C@](COC1CCC1)(CC(F)(F)F)NC(=O)c1cnc2c(F)cccc2c1] | 1.09 | 385 | G | |
| E.015 | 8-fluoro-N-[3,3,3-trifluoro-1-methyl-1-[(1-methylcyclo-hexoxy)methyl]-propyl]quinoline-3-carboxamide | 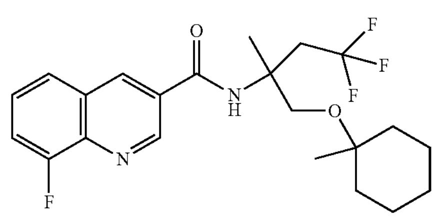 [SMILES: CC(COC1(C)CCCCC1)(CC(F)(F)F)NC(=O)c1cnc2c(F)cccc2c1] | 1.24 | 427 | G | |
| E.016 | N-[(1R)-1-(cyclo-hexoxymethyl)-3,3,3-trifluoro-1-methyl-propyl]-8-fluoro-quinoline-3-carboxamide | 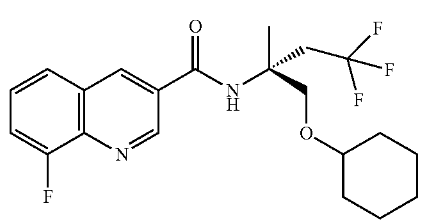 [SMILES: C[C@](COC1CCCCC1)(CC(F)(F)F)NC(=O)c1cnc2c(F)cccc2c1] | 1.19 | 413 | G | 80-85 |

TABLE E-continued

Physical data of compounds of formula (I)

| Entry | IUPAC Name | Structure | RT (min) | [M + H] (measured) | Method | MP ° C. |
|---|---|---|---|---|---|---|
| E.017 | N-[(1S)-1-(cyclo-hexoxymethyl)-3,3,3-trifluoro-1-methyl-propyl]-8-fluoro-quinoline-3-carboxamide | 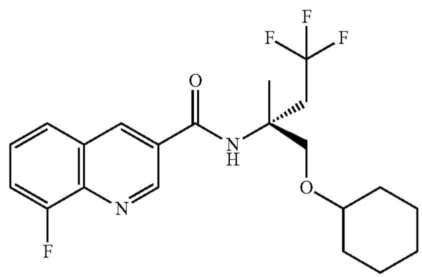 [SMILES: C[C@](COC1CCCCC1)(CC(F)(F)F)NC(=O)c1cnc2c(F)cccc2c1] | 1.19 | 413 | G | 80-85 |
| E.018 | N-[1-(benzyloxy-methyl)-1-methyl-2-(1-methylcyclo-propyl)ethyl]-8-fluoro-quinoline-3-carboxamide | 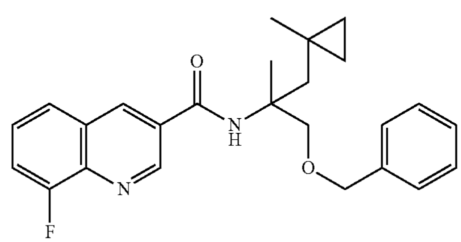 [SMILES: CC1(CC(C)(COCc2ccccc2)NC(=O)c2cnc3c(F)cccc3c2)CC1] | 1.17 | 407 | G | |
| E.019 | 8-fluoro-N-[3,3,3-trifluoro-1-methyl-1-(phenoxy-methyl)propyl]-quinoline-3-carboxamide | 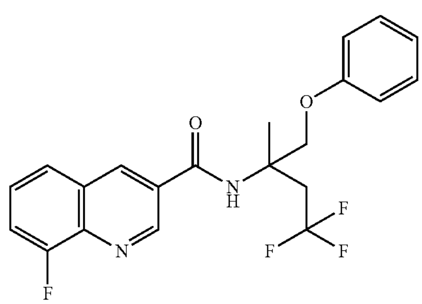 [SMILES: CC(COc1ccccc1)(CC(F)(F)F)NC(=O)c1cnc2c(F)cccc2c1] | 1.09 | 407 | G | |
| E.020 | N-[1,3-dimethyl-1-(2-methylallyloxy-methyl)butyl]-8-fluoro-quinoline-3-carboxamide | 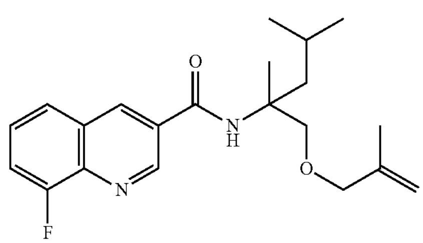 [SMILES: C=C(C)COCC(C)(CC(C)C)NC(=O)c1cnc2c(F)cccc2c1] | 1.14 | 360 | G | |
| E.021 | N-[1-(cyclobutoxy-methyl)-3,3,3-trifluoro-1-methyl-propyl]-8-fluoro-quinoline-3-carboxamide | 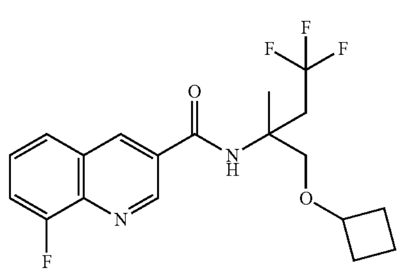 [SMILES: CC(COC1CCC1)(CC(F)(F)F)NC(=O)c1cnc2c(F)cccc2c1] | 1.09 | 385 | G | |

TABLE E-continued

Physical data of compounds of formula (I)

| Entry | IUPAC Name | Structure | RT (min) | [M + H] (measured) | Method | MP ° C. |
|---|---|---|---|---|---|---|
| E.022 | N-[1-(1-ethyl-propoxymethyl)-1,3-dimethyl-butyl]-8-fluoro-quinoline-3-carboxamide | 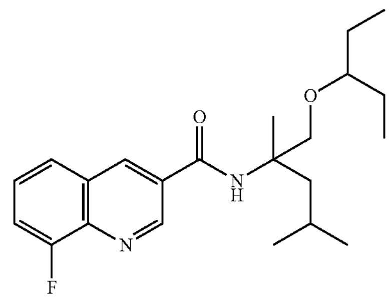 [SMILES: CCC(CC)OCC(C)(CC(C)C)NC(=O)c1cnc2c(F)cccc2c1] | 1.25 | 375 | G | |
| E.023 | N-[1-(cyclo-butoxymethyl)-1,3-dimethyl-butyl]-8-fluoro-quinoline-3-carboxamide | 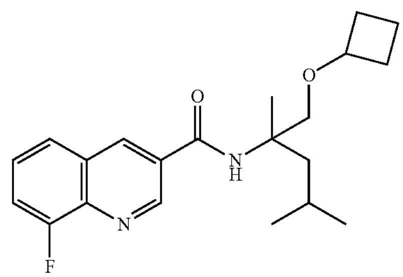 [SMILES: CC(C)CC(C)(COC1CCC1)NC(=O)c1cnc2c(F)cccc2c1] | 1.14 | 359 | G | |
| E.024 | 8-fluoro-N-[1-(iso-propoxymethyl)-1,3-dimethyl-butyl]quinoline-3-carboxamide | 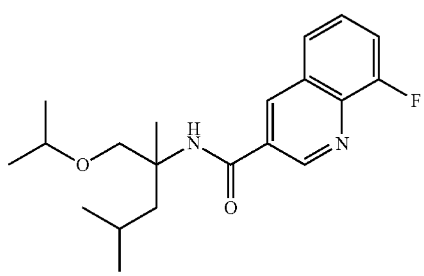 [SMILES: CC(C)CC(C)(COC(C)C)NC(=O)c1cnc2c(F)cccc2c1] | 1.12 | 347 | G | |
| E.025 | 8-fluoro-N-[1-(iso-butoxymethyl)-1,3-dimethyl-butyl]-quinoline-3-carboxamide | 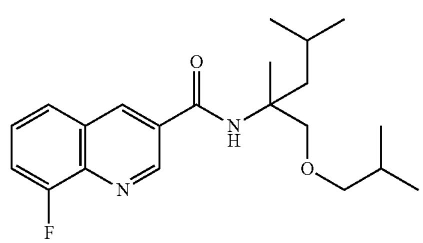 [SMILES: CC(C)COCC(C)(CC(C)C)NC(=O)c1cnc2c(F)cccc2c1] | 1.20 | 361 | G | |
| E.026 | N-[1-(cyclohept-oxymethyl)-3,3,3-trifluoro-1-methyl-propyl)-8-fluoro-quinoline-3-carboxamide | 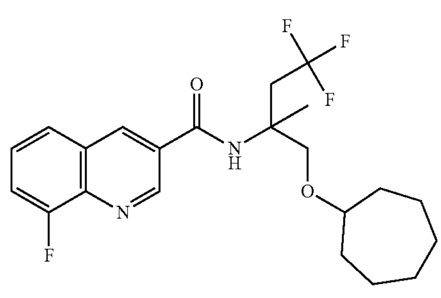 [SMILES: CC(COC1CCCCCC1)(CC(F)(F)F)NC(=O)c1cnc2c(F)cccc2c1] | 1.23 | 428 | G | 80-85 |

TABLE E-continued

Physical data of compounds of formula (I)

| Entry | IUPAC Name | Structure | RT (min) | [M + H] (measured) | Method | MP ° C. |
|---|---|---|---|---|---|---|
| E.027 | N-[1-(cyclohexoxy-methyl)-3,3,3-trifluoro-1-methyl-propyl]-8-fluoro-quinoline-3-carboxamide | 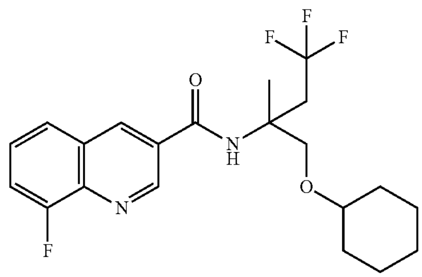 [SMILES: CC(COC1CCCCC1)(CC(F)(F)F)NC(=O)c1cnc2c(F)cccc2c1] | 1.19 | 413 | G | |
| E.028 | N-[1,3-dimethyl-1-(phenoxymethyl)-butyl]-8-fluoro-quinoline-3-carboxamide | 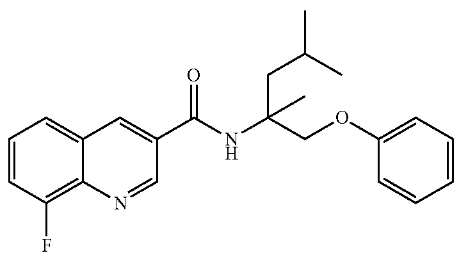 [SMILES: CC(C)CC(C)(COc1ccccc1)NC(=O)c1cnc2c(F)cccc2c1] | 1.17 | 395 | G | 120-122 |
| E.029 | N-[1-(cyclohexoxy-methyl)-1,3-dimethyl-butyl]-8-fluoro-quinoline-3-carboxamide | 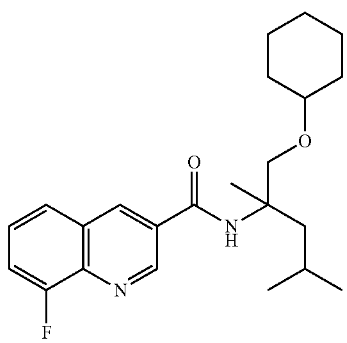 [SMILES: CC(C)CC(C)(COC1CCCCC1)NC(=O)c1cnc2c(F)cccc2c1] | 1.27 | 387 | G | |
| E.030 | N-[1-(benzyloxy-methyl)-1,3-dimethyl-butyl]-8-fluoro-quinoline-3-carboxamide | 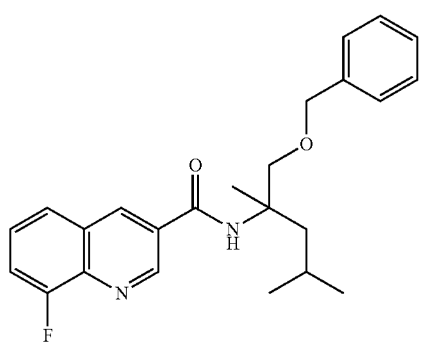 [SMILES: CC(C)CC(C)(COCc1ccccc1)NC(=O)c1cnc2c(F)cccc2c1] | 1.17 | 395 | G | 120-122 |
| E.031 | N-[1-(cyclopentoxy-methyl)-1,3-dimethyl-butyl]-8-fluoro-quinoline-3-carboxamide | 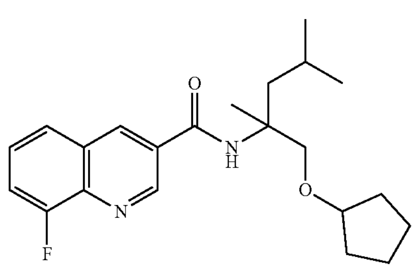 [SMILES: CC(C)CC(C)(COC1CCCC1)NC(=O)c1cnc2c(F)cccc2c1] | 1.23 | 373 | G | |

TABLE E-continued

Physical data of compounds of formula (I)

| Entry | IUPAC Name | Structure | RT (min) | [M + H] (measured) | Method | MP °C. |
|---|---|---|---|---|---|---|
| E.032 | 8-fluoro-N-[1-(methoxymethyl)-1,3-dimethyl-butyl]quinoline-3-carboxamide | 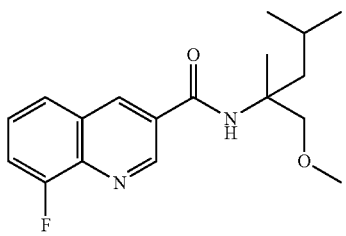 [SMILES: COCC(C)(CC(C)C)NC(=O)c1cnc2c(F)cccc2c1] | 0.98 | 319 | G | 136-138 |
| E.033 | 8-fluoro-N-[1-(methoxymethyl)-1-methyl-nonyl]-quinoline-3-carboxamide | 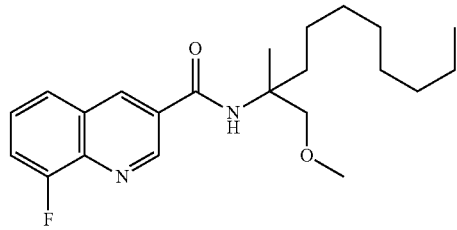 [SMILES: CCCCCCCCC(C)(COC)NC(=O)c1cnc2c(F)cccc2c1] | | | | |

Biological Examples

*Botryotinia fuckeliana* (*Botrytis cinerea*)/Liquid Culture (Gray Mould)

Conidia of the fungus from cryogenic storage are directly mixed into nutrient broth (Vogels broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

The following compounds gave at least 80% control of *Botryotinia fuckeliana* at 20 ppm when compared to untreated control under the same conditions, which showed extensive disease development:
E.001, E.002, E.003, E.004, E.005, E.006, E.007, E.008, E.009, E.010, E.011, E.012, E.013, E.0014, E.015, E.016, E.017, E.018, E.019, E.020, E.021, E.022, E.023, E.024, E.025, E.026, E.027, E.028, E.029, E.030, E.031, E.032, E.033

*Glomerella lagenarium* (*Colletotrichum lagenarium*)/Liquid Culture (Anthracnose)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is measured photometrically 3-4 days after application.

The following compounds gave at least 80% control of *Glomerella* lagenarium at 20 ppm when compared to untreated control under the same conditions, which showed extensive disease development:
E.001, E.002, E.003, E.004, E.005, E.006, E.007, E.008, E.009, E.010, E.011, E.012, E.013, E.014, E.015, E.016, E.017, E.019, E.020, E.021, E.022, E.023, E.024, E.025, E.026, E.027, E.0028, E.029, E.030, E.031, E.033

*Fusarium culmorum*/Liquid Culture (Head Blight)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

The following compounds gave at least 80% control of *Fusarium culmorum* at 20 ppm when compared to untreated control under the same conditions, which showed extensive disease development:
E.001, E.002, E.003, E.004, E.005, E.006, E.007, E.008, E.009, E.010, E.011, E.012, E.013, E.014, E.015, E.016, E.017, E.018, E.019, E.020, E.021, E.022, E.023, E.024, E.025, E.026, E.027, E.028, E.029, E.030, E.031, E.032, E.033

*Fusarium culmorum*/Wheat/Spikelet Preventative (Head Blight)

Wheat spikelets cv. Monsun are placed on agar in multiwell plates (24-well format) and sprayed with the formulated test compound diluted in water. The spikelets are inoculated with a spore suspension of the fungus 1 day after application. The inoculated spikelets are incubated at 20° C. and 60% rh under a light regime of 72 h semi darkness followed by 12 h light/12 h darkness in a climate chamber and the activity of a compound is assessed as percent disease control compared to untreated when an appropriate level of disease damage appears on untreated check spikelets (6-8 days after application).

The following compounds gave at least 80% control of *Fusarium culmorum* at 200 ppm when compared to untreated control under the same conditions, which showed extensive disease development:
E.001, E.002, E.003, E.004, E.005, E.006, E.007, E.008, E.010, E.011, E.012, E.013, E.014, E.016, E.017, E.019, E.020, E.022, E.023, E.024, E.025, E.026, E.027, E.028, E.029, E.031

*Gibberella zeae* (*Fusarium graminearum*)/Wheat/Spikelet Preventative (Head Blight)

Wheat spikelets cv. Monsun are placed on agar in multiwell plates (24-well format) and sprayed with the formulated test compound diluted in water. One day after application, the spikelets are inoculated with a spore suspension of the fungus. The inoculated test leaf disks are incubated at 20° C. and 60% rh under a light regime of 72 h semi darkness followed by 12 h light/12 h darkness in a climate chamber, the activity of a compound is assessed as percent disease control compared to untreated when an appropriate level of disease damage appears on untreated check spikelets (6-8 days after application).

The following compounds gave at least 80% control of *Gibberella zeae* at 200 ppm when compared to untreated control under the same conditions, which showed extensive disease development: E.001, E.003, E.007, E.008, E.010, E.012, E.014, E.017, E.019, E.020, E.023, E.024, E.025, E.027, E.033

*Monographella nivalis* (*Microdochium nivale*)/Liquid Culture (Foot Rot Cereals)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

The following compounds gave at least 80% control of *Monographella nivalis* at 20 ppm when compared to untreated control under the same conditions, which showed extensive disease development:

E.001, E.002, E.003, E.004, E.005, E.006, E.007, E.008, E.010, E.011, E.012, E.013, E.016, E.018, E.019, E.020, E.022, E.023, E.025, E.026, E.027, E.028, E.029, E.030, E.031, E.033

*Magnaporthe grisea* (*Pyricularia oryzae*)/Liquid Culture (Rice Blast)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

The following compounds gave at least 80% control of *Magnaporthe grisea* at 20 ppm when compared to untreated control under the same conditions, which showed extensive disease development:

E.001, E.002, E.003, E.004, E.005, E.006, E.007, E.008, E.009, E.011, E.012, E.015, E.016, E.017, E.018, E.019, E.020, E.021, E.022, E.023, E.024, E.025, E.026, E.027, E.029, E.030, E.031

What is claimed is:

1. A compound of formula (I)

(I)

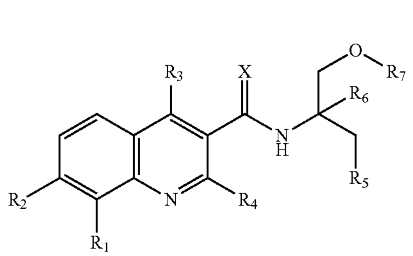

wherein

X is O or S;

$R_1$ is hydrogen, halogen, methyl or cyano;

$R_2$ is hydrogen, methyl or halogen;

$R_3$ and $R_4$ are each independently selected from hydrogen, halogen and methyl;

$R_5$ is $C_1$-$C_4$ alkyl, $C_1$-$C_2$ haloakyl, $C_2$-$C_4$ alkenyl or $C_3$-$C_6$ cycloalkyl, wherein the alkyl, alkenyl and cycloalkyl may be optionally substituted with 1 to 3 substituents independently selected from halogen, cyano, $C_1$-$C_3$ alkyl, $C_1$-$C_3$ alkoxy and $C_1$-$C_3$ alkylthio;

$R_6$ is hydrogen, cyano or $C_1$-$C_4$ alkyl;

$R_7$ is $C_1$-$C_5$ alkyl, $C_3$-$C_7$ cycloalkyl, $C_3$-$C_5$ alkenyl, $C_3$-$C_6$ cycloalkenyl, $C_3$-$C_5$ alkynyl, a $C_5$-$C_{10}$ saturated or partially unsaturated bicyclic carbocycle, aryl, aryl($C_1$-$C_4$)alkyl, a saturated or partially unsaturated heterocycle or heteroaryl, wherein the alkyl, cycloalkyl, alkenyl, cycloalkenyl, carbocycle, alkynyl, may be optionally substituted with one or more substituents independently selected from halogen, cyano, $C_1$-$C_3$ alkyl, $C_1$-$C_3$ alkoxy, $C_1$-$C_3$ alkylthio; $C_1$-$C_3$ haloalkoxy, $C_1$-$C_3$ haloalkylthio, $C_3$-$C_5$ cycloalkyl or phenyl, and wherein the aryl, heterocycle or heteroaryl may be optionally substituted with one or more substituents independently selected from halogen, cyano, $C_1$-$C_3$ alkyl, $C_1$-$C_3$ alkoxy, $C_1$-$C_3$ alkylthio; $C_1$-$C_3$ haloalkoxy, $C_1$-$C_3$ haloalkylthio or $C_3$-$C_5$ cycloalkyl;

or a salt or N-oxide thereof.

2. The compound according to claim 1 wherein $R_1$ is hydrogen, fluoro, chloro, bromo or methyl.

3. The compound according to claim 1 wherein $R_2$ is hydrogen, methyl, chloro or fluoro.

4. The compound according to claim 1 wherein $R_3$ and $R_4$ are each independently selected from hydrogen, chloro and methyl.

5. The compound according to claim 1 wherein $R_5$ is $C_1$-$C_4$ alkyl, $C_1$-$C_2$ haloakyl, $C_2$-$C_4$ alkenyl or $C_3$-$C_6$ cycloalkyl, wherein the alkyl, alkenyl and cycloalkyl may be optionally substituted with 1 to 3 substituents independently selected from fluoro, cyano, methyl, methoxy and methylthio.

6. The compound according to claim 1 wherein $R_6$ is hydrogen or $C_1$-$C_3$ alkyl.

7. The compound according to claim 1 wherein $R_7$ is $C_1$-$C_5$ alkyl, $C_3$-$C_7$ cycloalkyl, $C_3$-$C_5$ alkenyl, $C_3$-$C_6$ cycloalkenyl, $C_3$-$C_5$ alkynyl, a $C_5$-$C_{10}$ saturated bicyclic carbocycle, a $C_5$-$C_{10}$ partially unsaturated bicyclic carbocycle, phenyl, phenyl($C_1$-$C_3$)alkyl, oxetanyl, tetrahydrofuranyl, tetrahydropyranyl, pyridinyl, thiophenyl, thiazolyl, oxazolyl or pyrazolyl, wherein the alkyl, cycloalkyl, alkenyl, cycloalkenyl, carbocycle and alkynyl may be optionally substituted with one or more substituents independently selected from fluoro, chloro, cyano, methyl, methoxy, methylthio; $C_1$-$C_2$ fluoroalkoxy, $C_1$-$C_2$ fluoroalkylthio, cyclopropyl and cyclobutyl, and wherein the phenyl, oxetanyl, tetrahydrofuranyl, tetrahydropyranyl, pyridinyl, thiophenyl, thiazolyl, oxazolyl and pyrazolyl may be optionally substituted with one or more substituents independently selected from fluoro, chloro, cyano, methyl, methoxy, methylthio; $C_1$-$C_2$ fluoroalkoxy, $C_1$-$C_2$ fluoroalkylthio, cyclopropyl and cyclobutyl.

8. The compound according to claim 1 wherein $R_1$ is fluoro, chloro or methyl; $R_2$ is hydrogen or fluoro; $R_3$ and $R_4$ are each independently selected from hydrogen and methyl; $R_5$ is $C_1$-$C_4$ alkyl, $C_1$-haloakyl, $C_2$-$C_4$ alkenyl or $C_3$-$C_4$ cycloalkyl, wherein the alkyl, alkenyl and cycloalkyl may be optionally substituted with 1 to 3 substituents independently selected from fluoro, cyano and methyl; and $R_6$ is hydrogen, methyl or ethyl.

9. The compound according to claim 1 wherein $R_7$ is $C_1$-$C_8$ alkyl, $C_3$-$C_7$ cycloalkyl, $C_3$-$C_4$ alkenyl, $C_3$-$C_6$ cycloalkenyl, a $C_6$-$C_8$ saturated bicyclic carbocycle, a $C_6$-$C_8$ partially unsaturated bicyclic carbocycle, phenyl, phenyl ($C_1$-$C_3$)alkyl, pyridinyl, thiophenyl, thiazolyl, oxazolyl and pyrazolyl wherein the alkyl, cycloalkyl, alkenyl, cycloalkenyl and carbocycle may be optionally substituted with 1 to 3 substituents independently selected from fluoro, chloro, cyano, methyl, methoxy, methylthio, cyclopropyl and cyclobutyl, and wherein the phenyl, pyridinyl, thiophenyl, thiazolyl, oxazolyl and pyrazolyl may be optionally substituted with 1 to 3 of substituents independently selected from fluoro, chloro, cyano, methyl and cyclopropyl.

10. The compound according to claim 1 wherein X is O or S; $R_1$ is fluoro, chloro or methyl; $R_2$ is hydrogen or fluoro; $R_3$ and $R_4$ are each independently selected from hydrogen and methyl; $R_5$ is $C_1$-$C_4$ alkyl, $C_1$-haloakyl, $C_2$-$C_4$ alkenyl or $C_3$-$C_4$ cycloalkyl, wherein the alkyl, alkenyl and cycloalkyl may be optionally substituted with 1 to 3 substituents independently selected from fluoro, cyano and methyl; $R_6$ is hydrogen, methyl or ethyl; $R_7$ is $C_1$-$C_5$ alkyl, $C_3$-$C_7$ cycloalkyl, $C_3$-$C_4$ alkenyl, $C_3$-$C_6$ cycloalkenyl, a $C_6$-$C_8$ saturated bicyclic carbocycle, a $C_6$-$C_8$ partially unsaturated bicyclic carbocycle, phenyl, phenyl($C_1$-$C_3$)alkyl, pyridinyl, thiophenyl, thiazolyl, oxazolyl and pyrazolyl wherein the alkyl, cycloalkyl, alkenyl, cycloalkenyl and carbocycle may be optionally substituted with 1 to 3 substituents independently selected from fluoro, chloro, cyano, methyl, methoxy, methylthio, cyclopropyl and cyclobutyl, and wherein the phenyl, pyridinyl, thiophenyl, thiazolyl, oxazolyl and pyrazolyl may be optionally substituted with 1 to 3 of substituents independently selected from fluoro, chloro, cyano, methyl and cyclopropyl; or a salt or N-oxide thereof.

11. The compound according to claim 1 wherein X is O or S; $R_1$ is fluoro or methyl; $R_2$ is hydrogen; $R_3$ is methyl and $R_4$ is hydrogen; or $R_3$ is hydrogen and $R_4$ is methyl; or $R_3$ is hydrogen and $R_4$ is hydrogen; $R_5$ is $C_1$-$C_4$ alkyl, trifluoromethyl, $C_2$-$C_4$ alkenyl or $C_3$-$C_4$ cycloalkyl, wherein the alkyl, alkenyl and cycloalkyl may be optionally substituted with 1 to 3 fluorine atoms or a methyl; $R_6$ is methyl; $R_7$ is $C_3$-$C_5$ alkyl, $C_3$-$C_7$ cycloalkyl, $C_3$-$C_4$ alkenyl, a $C_6$-$C_8$ saturated bicyclic carbocycle, phenyl, phenyl($C_1$-$C_2$)alkyl or pyridyl, wherein the alkyl, cycloalkyl, alkenyl and carbocycle may be optionally substituted with 1 to 3 substituents independently selected from fluoro and methyl or 1 or 2 substituents independently selected from cyclopropyl and cyclobutyl, and wherein the phenyl and pyridyl may be optionally substituted with 1 to 2 substituents independently selected from fluoro, chloro and methyl; or a salt or N-oxide thereof.

12. The compound according to claim 1 wherein X is O.

13. A composition comprising a fungicidally effective amount of a compound of formula (I) as defined in claim 1.

14. The composition according to claim 13, wherein the composition further comprises at least one additional active ingredient and/or a diluent.

15. A method of combating, preventing or controlling phytopathogenic fungi which comprises applying to phytopathogenic fungi, to the locus of phytopathogenic fungi, or to a plant susceptible to attack by phytopathogenic fungi, or to propagation material thereof, a fungicidally effective amount of a compound of formula (I) as defined in claim 1.

16. A compound selected from the group consisting of:
N-[1-(2,2-dimethylpropoxymethyl)-3,3,3-trifluoro-1-methyl-propyl]-8-fluoro-quinoline-3-carboxamide;
8-chloro-N-[1-[(3,3-dimethylcyclobutoxy)methyl]-3,3,3-trifluoro-1-methyl-propyl]quinoline-3-carboxamide;
N-[1-[(4,4-difluorocyclohexoxy)methyl]-3,3,3-trifluoro-1-methyl-propyl]-8-fluoro-quinoline-3-carboxamide;
N-[1-[(3,3-dimethylcyclobutoxy)methyl]-3,3,3-trifluoro-1-methyl-propyl]-8-fluoro-quinoline-3-carboxamide;
N-[1-[(4-chlorophenoxy)methyl]-3,3,3-trifluoro-1-methyl-propyl]-8-fluoro-quinoline-3-carboxamide;
N-[1-(cyclopropylmethoxymethyl)-1,3,3-trimethyl-butyl]-8-fluoro-quinoline-3-carboxamide;
N-[1-(cyclobutoxymethyl)-3,3,3-trifluoro-1-methyl-propyl]-8-fluoro-4-methyl-quinoline-3-carboxamide;
N-[1-(cyclobutoxymethyl)-3,3,3-trifluoro-1-methyl-propyl]-7,8-difluoro-quinoline-3-carboxamide;
N-[1-(cyclobutoxymethyl)-3,3,3-trifluoro-1-methyl-propyl]-8-fluoro-2-methyl-quinoline-3-carboxamide;
8-fluoro-N-[3,3,3-trifluoro-1-methyl-1-[(1-methylcyclopentoxy)methyl]propyl]quinoline-3-carboxamide;
N-[1-(cyclobutoxymethyl)-3,3,3-trifluoro-1-methyl-propyl]-8-methyl-quinoline-3-carboxamide;
8-chloro-N-[1-(cyclobutoxymethyl)-3,3,3-trifluoro-1-methyl-propyl]quinoline-3-carboxamide;
N-[(1S)-1-(cyclobutoxymethyl)-3,3,3-trifluoro-1-methyl-propyl]-8-fluoro-quinoline-3-carboxamide;
N-[(1S)-1-(cyclobutoxymethyl)-3,3,3-trifluoro-1-methyl-propyl]-8-fluoro-quinoline-3-carboxamide;
8-fluoro-N-[3,3,3-trifluoro-1-methyl-1-[(1-methylcyclohexoxy)methyl]propyl]quinoline-3-carboxamide;
N-[(1R)-1-(cyclohexoxymethyl)-3,3,3-trifluoro-1-methyl-propyl]-8-fluoro-quinoline-3-carboxamide;
N-[(1S)-1-(cyclohexoxymethyl)-3,3,3-trifluoro-1-methyl-propyl]-8-fluoro-quinoline-3-carboxamide;
N-[1-(benzyloxymethyl)-1-methyl-2-(1-methylcyclopropyl)ethyl]-8-fluoro-quinoline-3-carboxamide;
8-fluoro-N-[3,3,3-trifluoro-1-methyl-1-(phenoxymethyl)propyl]quinoline-3-carboxamide;
N-[1,3-dimethyl-1-(2-methylallyloxymethyl)butyl]-8-fluoro-quinoline-3-carboxamide;
N-[1-(cyclobutoxymethyl)-3,3,3-trifluoro-1-methyl-propyl]-8-fluoro-quinoline-3-carboxamide;
N-[1-(1-ethylpropoxymethyl)-1,3-dimethyl-butyl]-8-fluoro-quinoline-3-carboxamide;
N-[1-(cyclobutoxymethyl)-1,3-dimethyl-butyl]-8-fluoro-quinoline-3-carboxamide;
8-fluoro-N-[1-(isopropoxymethyl)-1,3-dimethyl-butyl]quinoline-3-carboxamide;
8-fluoro-N-[1-(isobutoxymethyl)-1,3-dimethyl-butyl]quinoline-3-carboxamide;
N-[1-(cycloheptoxymethyl)-3,3,3-trifluoro-1-methyl-propyl]-8-fluoro-quinoline-3-carboxamide;
N-[1-(cyclohexoxymethyl)-3,3,3-trifluoro-1-methyl-propyl]-8-fluoro-quinoline-3-carboxamide;
N-[1,3-dimethyl-1-(phenoxymethyl)butyl]-8-fluoro-quinoline-3-carboxamide;
N-[1-(cyclohexoxymethyl)-1,3-dimethyl-butyl]-8-fluoro-quinoline-3-carboxamide;
N-[1-(benzyloxymethyl)-1,3-dimethyl-butyl]-8-fluoro-quinoline-3-carboxamide;
N-[1-(cyclopentoxymethyl)-1,3-dimethyl-butyl]-8-fluoro-quinoline-3-carboxamide;
8-fluoro-N-[1-(methoxymethyl)-1,3-dimethyl-butyl]quinoline-3-carboxamide; and
8-fluoro-N-[1-(methoxymethyl)-1-methyl-nonyl]quinoline-3-carboxamide.

17. The compound of claim 16, wherein the compound is selected from the group consisting of:
8-fluoro-N-[1-(isopropoxymethyl)-1,3-dimethyl-butyl]quinoline-3-carboxamide;
8-fluoro-N-[1-(isobutoxymethyl)-1,3-dimethyl-butyl]quinoline-3-carboxamide;

N-[1-(cycloheptoxymethyl)-3,3,3-trifluoro-1-methyl-propyl]-8-fluoro-quinoline-3-carboxamide;
N-[1-(cyclohexoxymethyl)-3,3,3-trifluoro-1-methyl-propyl]-8-fluoro-quinoline-3-carboxamide;
N-[1,3-dimethyl-1-(phenoxymethyl)butyl]-8-fluoro-quinoline-3-carboxamide;
N-[1-(cyclohexoxymethyl)-1,3-dimethyl-butyl]-8-fluoro-quinoline-3-carboxamide;
N-[1-(benzyloxymethyl)-1,3-dimethyl-butyl]-8-fluoro-quinoline-3-carboxamide;
N-[1-(cyclopentoxymethyl)-1,3-dimethyl-butyl]-8-fluoro-quinoline-3-carboxamide;
8-fluoro-N-[1-(methoxymethyl)-1,3-dimethyl-butyl]quinoline-3-carboxamide; and
8-fluoro-N-[1-(methoxymethyl)-1-methyl-nonyl]quinoline-3-carboxamide.

18. The compound of claim 16, wherein the compound is selected from the group consisting of:
8-chloro-N-[1-(cyclobutoxymethyl)-3,3,3-trifluoro-1-methyl-propyl]quinoline-3-carboxamide;
N-[(1S)-1-(cyclobutoxymethyl)-3,3,3-trifluoro-1-methyl-propyl]-8-fluoro-quinoline-3-carboxamide;
N-[(1S)-1-(cyclobutoxymethyl)-3,3,3-trifluoro-1-methyl-propyl]-8-fluoro-quinoline-3-carboxamide;
8-fluoro-N-[3,3,3-trifluoro-1-methyl-1-[(1-methylcyclohexoxy)methyl]propyl]quinoline-3-carboxamide;
N-[(1R)-1-(cyclohexoxymethyl)-3,3,3-trifluoro-1-methyl-propyl]-8-fluoro-quinoline-3-carboxamide;
N-[(1S)-1-(cyclohexoxymethyl)-3,3,3-trifluoro-1-methyl-propyl]-8-fluoro-quinoline-3-carboxamide;
N-[1-(benzyloxymethyl)-1-methyl-2-(1-methylcyclopropyl)ethyl]-8-fluoro-quinoline-3-carboxamide;
8-fluoro-N-[3,3,3-trifluoro-1-methyl-1-(phenoxymethyl)propyl]quinoline-3-carboxamide;
N-[1,3-dimethyl-1-(2-methylallyloxymethyl)butyl]-8-fluoro-quinoline-3-carboxamide;
N-[1-(cyclobutoxymethyl)-3,3,3-trifluoro-1-methyl-propyl]-8-fluoro-quinoline-3-carboxamide;
N-[1-(1-ethylpropoxymethyl)-1,3-dimethyl-butyl]-8-fluoro-quinoline-3-carboxamide; and
N-[1-(cyclobutoxymethyl)-1,3-dimethyl-butyl]-8-fluoro-quinoline-3-carboxamide.

19. The compound of claim 16, wherein the compound is selected from the group consisting of:
N-[1-(2,2-dimethylpropoxymethyl)-3,3,3-trifluoro-1-methyl-propyl]-8-fluoro-quinoline-3-carboxamide;
8-chloro-N-[1-[(3,3-dimethylcyclobutoxy)methyl]-3,3,3-trifluoro-1-methyl-propyl]quinoline-3-carboxamide;
N-[1-[(4,4-difluorocyclohexoxy)methyl]-3,3,3-trifluoro-1-methyl-propyl]-8-fluoro-quinoline-3-carboxamide;
N-[1-[(3,3-dimethylcyclobutoxy)methyl]-3,3,3-trifluoro-1-methyl-propyl]-8-fluoro-quinoline-3-carboxamide;
N-[1-[(4-chlorophenoxy)methyl]-3,3,3-trifluoro-1-methyl-propyl]-8-fluoro-quinoline-3-carboxamide;
N-[1-(cyclopropylmethoxymethyl)-1,3,3-trimethyl-butyl]-8-fluoro-quinoline-3-carboxamide;
N-[1-(cyclobutoxymethyl)-3,3,3-trifluoro-1-methyl-propyl]-8-fluoro-4-methyl-quinoline-3-carboxamide;
N-[1-(cyclobutoxymethyl)-3,3,3-trifluoro-1-methyl-propyl]-7,8-difluoro-quinoline-3-carboxamide;
N-[1-(cyclobutoxymethyl)-3,3,3-trifluoro-1-methyl-propyl]-8-fluoro-2-methyl-quinoline-3-carboxamide;
8-fluoro-N-[3,3,3-trifluoro-1-methyl-1-[(1-methylcyclopentoxy)methyl]propyl]quinoline-3-carboxamide; and
N-[1-(cyclobutoxymethyl)-3,3,3-trifluoro-1-methyl-propyl]-8-methyl-quinoline-3-carboxamide.

\* \* \* \* \*

UNITED STATES PATENT AND TRADEMARK OFFICE
CERTIFICATE OF CORRECTION

PATENT NO. : 11,185,073 B2
APPLICATION NO. : 16/641151
DATED : November 30, 2021
INVENTOR(S) : Matthias Weiss et al.

Page 1 of 1

It is certified that error appears in the above-identified patent and that said Letters Patent is hereby corrected as shown below:

In the Specification

At Column 15, Line 10, " " should read -- --

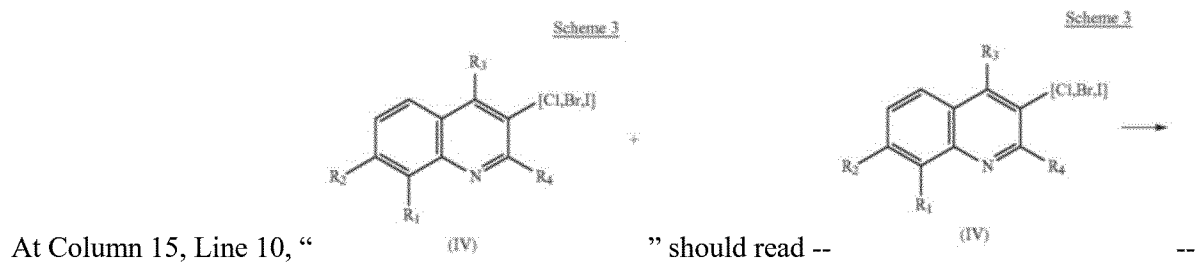

Signed and Sealed this
Fifteenth Day of March, 2022

Drew Hirshfeld
*Performing the Functions and Duties of the
Under Secretary of Commerce for Intellectual Property and
Director of the United States Patent and Trademark Office*